United States Patent [19]

Smith et al.

[11] Patent Number: 5,767,399
[45] Date of Patent: Jun. 16, 1998

[54] METHOD OF ASSAYING COMPRESSIVE STRENGTH OF ROCK

[75] Inventors: Lee Morgan Smith; William A. Goldman, both of Houston, Tex.

[73] Assignee: Dresser Industries, Inc., Dallas, Tex.

[21] Appl. No.: 621,412

[22] Filed: Mar. 25, 1996

[51] Int. Cl.$^6$ .................................................. E21B 49/02
[52] U.S. Cl. ........................................ 73/152.11; 364/422
[58] Field of Search ........................ 73/157.02, 152.05, 73/152.07, 152.11, 784, 788, 789, 790, 818, 821; 364/422

[56] References Cited

U.S. PATENT DOCUMENTS

| | | | |
|---|---|---|---|
| 4,064,749 | 12/1977 | Pittman et al. | 73/152.02 |
| 4,627,276 | 12/1986 | Burgess et al. | 73/152.44 |
| 4,685,329 | 8/1987 | Burgess | 73/152.44 |
| 4,914,591 | 4/1990 | Warren et al. | 364/422 |
| 4,981,037 | 1/1991 | Holbrook et al. | 175/50 X |
| 5,012,674 | 5/1991 | Millheim et al. | 73/818 X |
| 5,282,384 | 2/1994 | Holbrook | 73/152.05 |
| 5,415,030 | 5/1995 | Jogi et al. | 73/152.03 |
| 5,442,950 | 8/1995 | Unalmiser et al. | 73/152.05 X |
| 5,449,047 | 9/1995 | Shivley, Jr. | 175/27 |

FOREIGN PATENT DOCUMENTS 0 466 255 A2   1/1992   European Pat. Off. .

OTHER PUBLICATIONS

Philip Holbrook, Michael Hauck; Petrophysical—Mechanical Math Model Real–time Wellsite Poor Pressure/Fracture Gradient Prediction . *Society of Petroleum Engineers (STE)* Pub. No. 16666, Published Sep., 1987 in Dallas, Texas.

Kenneth L. Mason; 3–Cone Bit Selection with Sonic Logs pp. 135–142, *SPE Drilling Engineering*, Jun. 1987, first published Sep. 1984 in Houston, Texas.

Geir Hareland and L.L. Hoeberock; Use of Drilling Parameters to Predict In–Situ Stress Bounds pp. 457–471, *SPE/IADC 27527*, 1993..

E.C. Onyia; Relationships Between Formation Strength, Drilling Strength, and Electric Log Properties pp. 605–618, *SPE Drilling Engineering*, 1988.

R.C. Pessier, M.J. Fear; Quantifying Common Drilling Problems with Mechanical Specific Energy and Bit–Specific Coeffecient of Sliding Friction pp. 373–388, *SPE Paper 24584*, published Oct. 1982, Washington, D.C.

J.P.R. Sparr and L.W. Ledgerwood, Harvey Goodman, R.L. Graff and T.J. Moo; Formation Compressive Strength Estimates for Predicting Drillability and PDC Bit Selection pp 569–578, *SPE/IADC 29397*, published Feb. 1995, Amsterdam, Netherlands.

Allen D. Gault; Measurement of Drilling Properties pp. 143–148, *SPE Drilling Engineer*, Jun. 1987, published New Orleans, Louisiana (Mar. 1985).

*Primary Examiner*—Michael Brock
*Attorney, Agent, or Firm*—Browning Bushman

[57] ABSTRACT

A method of assaying the compressive strength of rock comprises testing a primary plurality of rock samples of similar lithology, at least some of which have different porosities, to determine, for each sample respectively, a value corresponding to compressive strength and a value corresponding to porosity. A first series of pairs of electrical compressive strength and porosity signals, the signals of each pair corresponding, respectively, to the compressive strength and porosity values for a respective one of the samples, is generated. These signals are processed by a computer to extrapolate additional such pairs of signals and generate a second series of electrical signals corresponding to compressive strength as a function of porosity. The second series of signals may correspond to unconfined compressive strength, and may be further processed, to generate a cumulative series of signals, using electrical adjustment signals corresponding to other conditions affecting the compressive strength of the rock. Site characteristics of the rock for a wellbore locus, at a plurality of sites along the length of the locus, and as the rock would be addressed by a drill bit, are determined. At least one of these site characteristics is porosity. The site characteristics are used to generate a plurality of site signals, which, upon processing with the second series of signals (or cumulative series, if any), generate in-situ compressive strength signals corresponding to the in-situ compressive strengths of the rock at the respective sites.

60 Claims, 4 Drawing Sheets

METHOD OF ASSAYING COMPRESSIVE STRENGTH OF ROCK

BACKGROUND

The present invention pertains to the assaying of the compressive strength of rock, and is particularly applicable to the generation and/or modification of a plan for drilling a wellbore along a given locus.

Various schemes have been proposed for determining or projecting compressive strength of rock along a wellbore locus. In one such scheme, it is proposed to relate the compressive strength of the rock directly to the transit time of shear sonic logs. Shear logs are relatively expensive. Furthermore, since shear transit time is rarely measured in practice, it would usually have to be derived from the transit time of compressional sonic logs. Moreover, this method does not take into account porosity, the effect of confinement stress, or stress history, nor other relevant physical conditions such as dip angle and temperature. Finally, the accuracy of this method can be affected by microcracks in the rock formation.

Others have suggested back calculating rock strength using only the forces applied during drilling. These forces are rarely directly measured. Therefore they must usually be extrapolated from other parameters. Again, neither porosity, confinement stress, stress history, nor the other aforementioned physical properties which can effect compressive strength of the rock are taken into account.

In still another example, the rock strength is projected from the elastic modulus. This not only suffers from similar disadvantages as the other prior art described above, but in addition, is valid, at best, only for rock which has not been stressed beyond its elastic limit.

"Relationships Between Formation Strength, Drilling Strength, and Electric Log Properties," by E. C. Onyia, *Society of Petroleum Engineers*, Paper No. 18166, October 1988, does relate compressive strength to porosity but does not take into account differences in various kinds of lithology, e.g. sandstone as opposed to shale. It gives erroneous results near maximum or minimum porosity values, and like the other methods described above, fails to take stress history into account.

SUMMARY OF THE INVENTION

The present invention provides a method of assaying the compressive strength of rock, which method develops compressive strength as a function of porosity, and in addition is lithology specific.

In preferred embodiments, not only is stress history taken into account, but confinement stress, as well as other physical properties (such as temperature and bed plane orientation or "dip angle") are used to refine the assay. The assay may be used to determine the strength of the rock at various sites along the locus of a wellbore prior to and/or during the drilling of a wellbore along that locus.

More specifically, in its most basic form, the method of the present invention comprises the steps of testing a primary plurality of rock samples of similar lithology, at least some of which have different porosities, to determine, for each sample respectively, a compressive strength and a porosity.

From these test data, a first series of pairs of electrical signals is generated. Each pair of signals in this first series includes a compressive strength signal and a porosity signal, corresponding, respectively, to the compressive strength and porosity for a respective one of the primary rock samples. Using a computer, this first series of signals is processed to extrapolate additional such pairs of signals and generate a second series of electrical signals corresponding to compressive strength as a function of porosity.

Because the very process of collecting and preparing the rock samples stresses at least some of the rock in each sample, not only beyond its yield point or elastic limit, but beyond its ductility limit or uniaxial compressive strength value, preferred embodiments of the invention take the stress history of the samples into account in developing the aforementioned second series. This may be done by iteratively processing electrical signals potentially corresponding to certain characteristics to generate multiple potential second series, and using as the second series the potential second series corresponding to a function whose graphical representation in a logarithmic decline most nearly fitting the upper periphery of a cloud of data points corresponding to the first series of signals on a Cartesian graph of compressive strength versus porosity. In effect, this means that only the rock samples which have been least stressed by the collection and preparation process will be used in generating the second series.

In preferred embodiments, the compressive strength determined in the testing of the primary rock samples is unconfined compressive strength, and the second series of signals is adjusted by processing with adjustment signals to generate a cumulative series of signals which takes into account other conditions affecting compressive strength, these conditions preferably including confinement stress.

In order to generate stress adjustment signals for so adjusting to take confinement stress into account, a secondary plurality of rock samples of similar lithology to the primary samples, and at least some of which have different porosities, are tested under laterally confined conditions. Again, for each sample, a confined compressive strength and a porosity are determined. A third series of pairs of electrical confined compressive strength and porosity signals is generated and processed so as to extrapolate additional such pairs of signals and generate a fourth series of electrical signals corresponding to confined compressive strength as a function of porosity. This fourth series may be used as the cumulative series if there is no adjustment for still other conditions. Again, stress history may be taken into account by curve-fitting the graphical representation of the fourth series to the upper periphery of a cloud of data points corresponding to the third series.

The adjustment signals may also correspond to functions of changes in compressive strength due to other conditions, such as the dip angle of a bedding plane of the rock and/or temperature, once again with stress history taken into account.

In any event, the assay process is preferably repeated for at least one other lithology, and the two resulting cumulative series may then be used to model the in situ compressive strength of the rock at a plurality of sites along a wellbore locus through rock including such lithology(ies), in advance of drilling and/or in real time. This modeling, in turn, is used to generate and/or periodically revise a plan for drilling the well along that locus. The plan may include such factors as the choice of drill bit for drilling different sections of the well, choice of weight-on-bit and rotary speed, and possibly other factors. These other factors may even include the precise trajectory or locus of the well. Specifically, the modeled compressive strength may indicate that the well would be unstable, i.e. likely to cave in, at a particular spot along an originally proposed locus, and it may be possible, again using the modeled compressive strengths at various sites, to slightly alter the locus to avoid that problem.

Specific, and highly preferred, examples of such practical uses for the rock compressive strength assays produced in accord with the present invention are fully described in the present inventors' applications entitled "Method of Assaying Downhole Occurrences and Conditions," Ser. No. 08/621,411 and "Method of Regulating Drilling Conditions Applied to a Well Bit," Ser. No. 08/621,414, filed contemporaneously herewith, and hereby expressly incorporated by reference. However, it is emphasized that the rock compressive strength assays produced in accord with the present invention could also be used in other methods of drill bit selection, weight-on-bit and rotary speed selection, and determination of other well drilling plan factors. The rock strength assays could even be used simply for general guidance of the operation, based on his experience.

In any event, for the in-situ modeling, site characteristics of the rock for the wellbore locus, including porosity and other physical properties similar to those used to generate the aforementioned adjustment signals, are determined. Corresponding signals are generated and processed with the cumulative series to produce signals corresponding to in-situ compressive strengths of the rock at respective sites.

However, in order to produce the site signals, additional conditions peculiar to the locus are preferably taken into account. These may include the pressure differential between fluid in the wellbore and fluid in the surrounding formation ("overbalance"), the effective stress due to overburden, and/or the effective stress due to the local geological stress field.

Various other features and advantages of the present invention and/or its preferred embodiments will be made apparent by the following detailed description, the drawings, and the claims.

DETAILED DESCRIPTION

Before describing the invention per se, it is helpful to consider some of the characteristics of sedimentary rock when subjected to stress.

Figure 2:
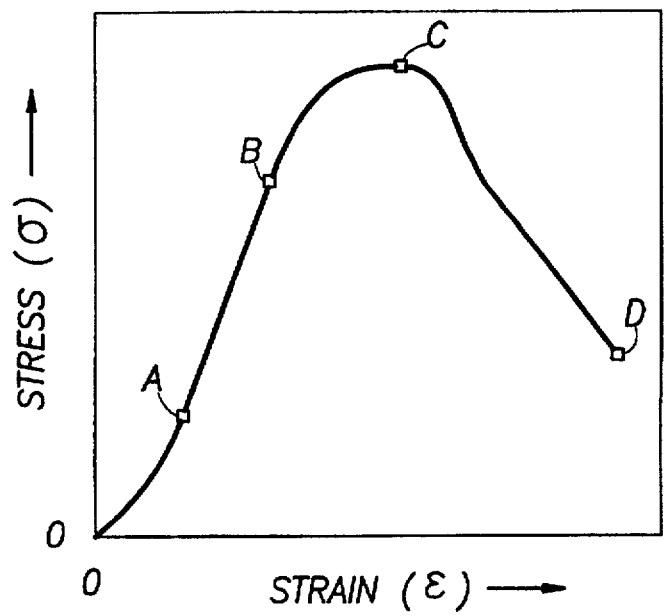
FIG. 2 is a graph illustrating the behavior of rock when subjected to stress.

A typical stress-strain curve for sedimentary rock is presented in FIG. 2. The curve exhibits four regions: OA, AB, BC, and CD. The stress value at point C is defined as the uniaxial compressive strength or ductility limit and is the maximum stress that a particular rock sample can sustain without damage (weakening). In the regions OA and AB the rock exhibits essentially elastic behavior. That is, stress loading and unloading in this region induces negligible permanent deformation. Point B, defined as the yield point or elastic limit, is an inflection point marking the transition from the elastic region OB to the ductile region BC. Stress loading a rock to its ductile region always induces a permanent deformation upon unloading and can cause failure. Reloading the rock will cause the curve to follow a different path that rejoins the original curve in the ductile region before point C. Although the rock is permanently deformed, it still retains its original strength (if it has not failed). In the ductile region BC, the rock can sustain permanent deformation without losing its ability to sustain maximum load (although, as mentioned, it does not always do so, but rather may fail). Region CD is defined as the brittle region. Here the rock's ability to sustain load decreases with increasing deformation. In other words, brittle rocks are permanently weakened, and successive load and unload cycles further weaken the rock. The formation of microcracks in the brittle region contributes to weakening of the rock matrix. A rock in the brittle region is in a state of progressive failure. At the value at point D, total failure will definitely occur, if it has not already done so.

Figure 1:
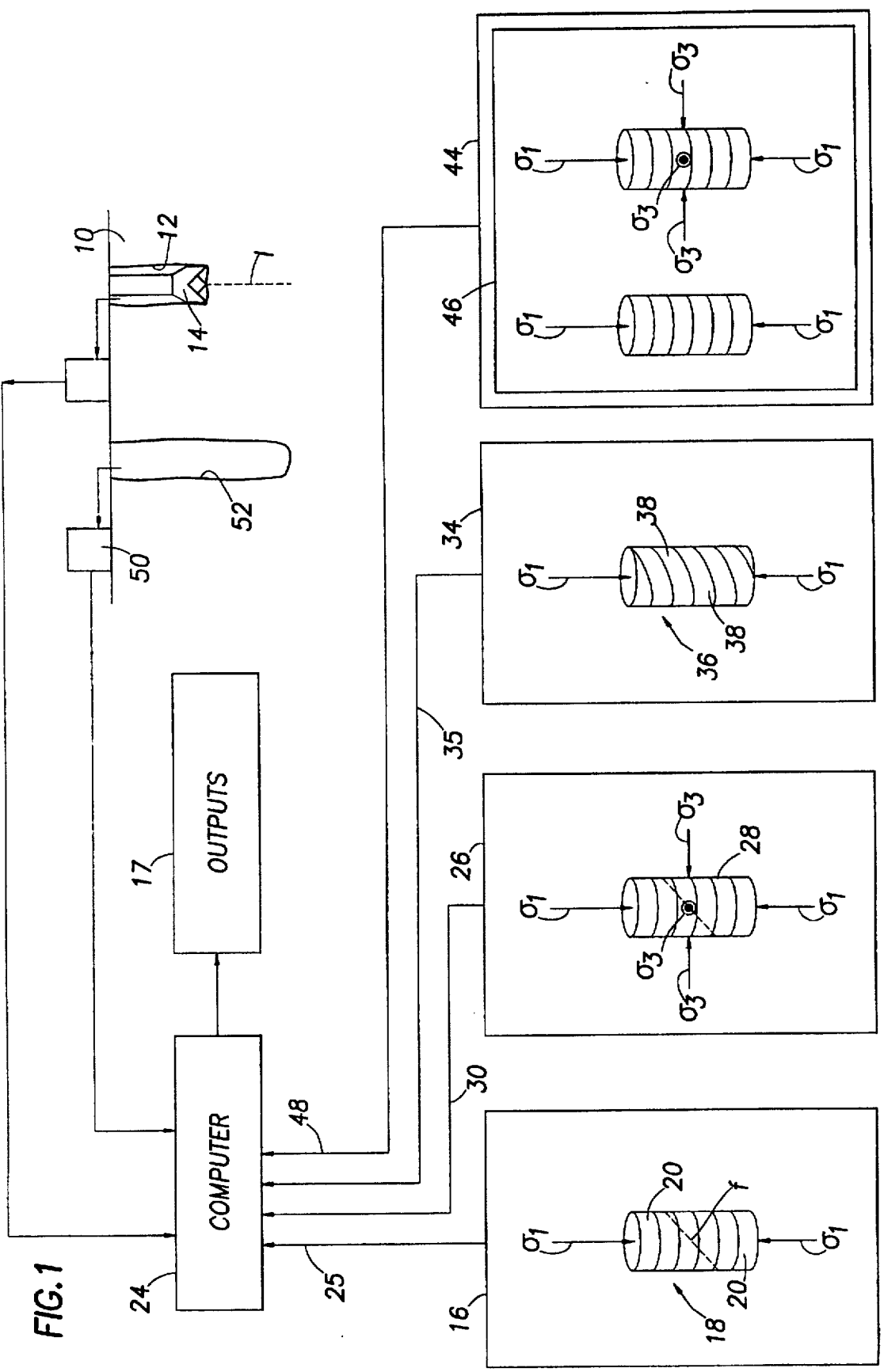
FIG. 1 is a schematic generally representing an exemplary embodiment of the present invention.

Turning now to the invention itself, and referring to FIG. 1, an exemplary embodiment will be described. This embodiment models the compressive strength of the rock along the locus of a wellbore. For convenience, there is illustrated a bit 14 which has begun to drill a wellbore 12 along that locus, the remainder of which is indicated by line l. However, as will be explained more fully below, the modeling method described could be performed in advance of beginning to drill and/or in real time as the well is being drilled.

In any event, prior to the actual modeling, at least one compressive strength assay is performed, in accord with the present invention. To perform such an assay, a primary plurality of rock samples of a lithology occurring along locus l is tested, as indicated at step box 16. The lithology of the samples tested at 16 is relatively pure, e.g. a true sandstone or a true shale, as one of skill in geology would classify naturally occurring rock. The lithology is also of a type anticipated along locus l. If desired, and if sufficient core samples are available from a particular field, the samples tested may be from the very field in which the well 14 is to be drilled, and the resulting assays on which modeling is to be based could be in the form of optimal local regression curves and corresponding signal series. However, the investigations to date in connection with developing the present invention have indicated that this is unnecessary, as lithologically similar samples from various locations tend to produce sufficiently identical results.

Only one exemplary sample 18 is shown in box 16, but it will be understood that the same type of test will be performed on each of the samples in the primary plurality. In particular, the testing in question will determine, for each sample, respectively, compressive strength and porosity. Porosity is determined by any one of several standard methods known in the art.

Compressive strength is determined by applying compressive force to the sample, parallel to the central axis of the sample, as indicated by the arrows in box 16 until the sample fails. The strength at which the sample fails is indicated herein by the symbol $\sigma_1$ and is the compressive strength of the sample. The sample will fail along an oblique plane f, characteristic of the lithology, and which is the plane of greatest stress. The primary plurality of samples is tested by unconfined compressive stress, and is therefore not laterally supported as the force $\sigma_1$ is being applied.

As shown, the samples are cylindrical, and for purposes of the testing done at step 1 6, are cut so that any strata or bed planes 20 thereof lie perpendicular to the axis of the cylinder. The core samples should be carefully cut and prepared to standard test dimensions, taking care to minimize damage to the samples. Other criteria for proper compressive strength testing are described in detail in any number of reference works available to those of skill in the art, and will not be reiterated in detail herein.

Since compressive strength is strongly dependent on intergranular cementation, and porosity is a measure of intergranular cementation, porosity is used herein as the primary criterion or variable for determining baseline compressive strength. This is not only more accurate than other criteria used in the prior art, but is easier and more practical, since, as mentioned, porosity is easily measured in laboratories, and is also routinely determined in the course of well drilling operations.

After all of the primary samples have been tested, and their respective unconfined compressive strengths and porosities determined, a first series of pairs of electrical compressive strength and porosity signals is generated for processing in computer 24 as indicated by line 25. The signals of each pair correspond, respectively, to the compressive strength and porosity for a respective one of the primary samples.

Figure 3:
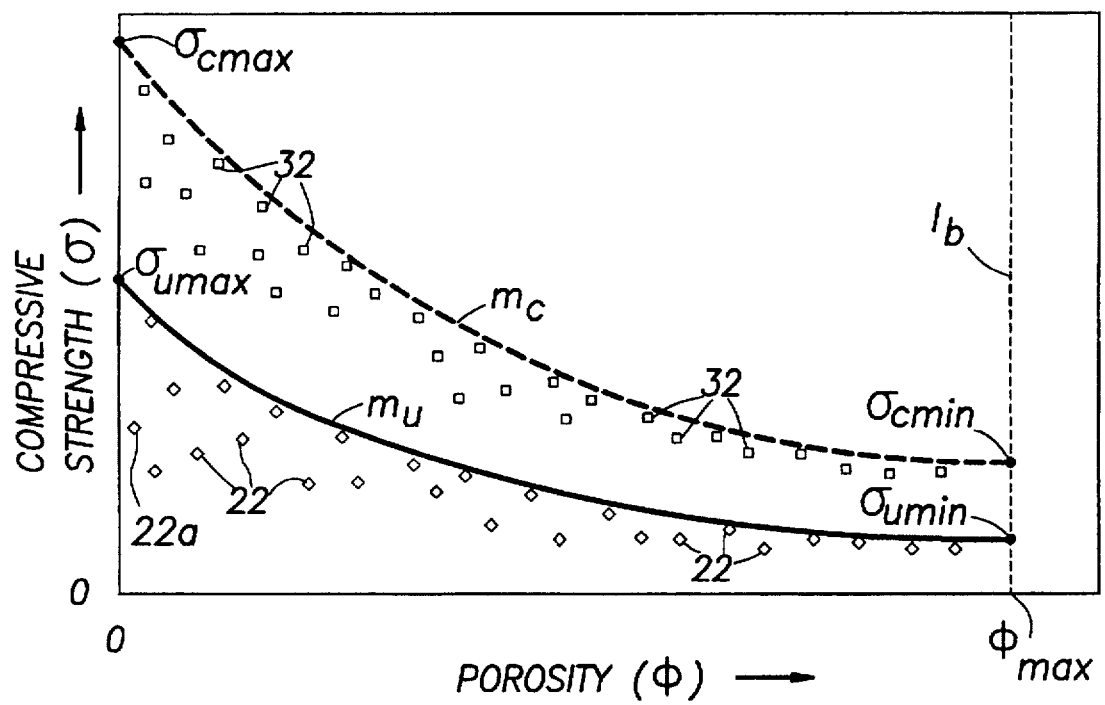
FIG. 3 is a graphical representation of first, second, third and fourth series of electrical signals.

Referring to FIG. 3, the lower "cloud" of solid data points 22 correspond to the paired porosities and compressive strengths for respective primary samples, as related to a Cartesian graph of compressive strength versus porosity.

(Throughout this specification, whenever there is reference to numerical values and/or their graphical representations, and/or to calculations or other manipulations of those values or representations, it should be understood that those manipulations may be performed by processing corresponding electrical signals using a suitably programmed or configured computer, such as 24.) Referring to FIG. 3, it will be seen that samples of very similar porosity test out at different compressive strengths. This is because, in obtaining and preparing the samples, it is inevitably necessary to stress at least some of the rock of each sample, i.e. at least that near the periphery of the sample, to its uniaxial compressive strength or ductility limit (refer again to C in FIG. 2); and some samples will be so stressed more than others. This damage is generally referred to herein as "stress history" of the samples.

An initial goal at this stage of the method is for a computer 24, appropriately configured or programmed in a manner to be described more fully below, to process the paired signals 22 of the first series to extrapolate additional such pairs of signals and generate a second series of electrical signals corresponding to unconfined compressive strength as a function of porosity.

In typical prior art methods, whether relying on porosity or any other basic criterion, it has generally been the practice, when presented with such a "cloud" of data points, to generate a function which graphically illustrates as a curve passing through the vertical center of the cloud. However, in accord with the present invention, in order to correct for the aforementioned stress history occurring in the process of collecting and/or preparing the samples, the second series is such that it will graphically illustrate as a curve $m_u$, which passes generally along the upper periphery of the cloud of data points 22. (As used herein, "corresponding to" will mean functionally related to, whether relating a signal to a physical phenomenon (or value), a signal to another signal, or a physical phenomenon (or value) to another physical phenomenon (or value); in the case of relating a signal to a physical phenomenon, "corresponding precisely to" will mean that the signal translates or converts precisely to the value of the phenomenon or datum in question.)

In the present invention, it has been found that the curve in $m_u$ will be generally of the form:

$$\sigma_u = S_e \sigma_{umax} + (1-S_e)\sigma_{umin} \tag{1}$$

where:

$$S_e = (1-\phi/\phi_{max})^\alpha \tag{2}$$

$\sigma_u$=unconfined compressive strength $\sigma_{umax}$=maximum unconfined compressive strength (at zero porosity)

$\sigma_{umin}$=minimum unconfined compressive strength (at maximum porosity)

$\phi$=porosity $\phi_{max}$=maximum porosity $\alpha$=a mineralogy value.

It is noted that $S_e$ is defined as the "effective solidity." Equation (2) is a convenient mathematical definition because, theoretically, if the porosity of the rock were ever to reach a maximum value, there would be no intergranular cementation, and consequently zero compressive strength; in other words, the rock would disintegrate; the formula given above for $S_e$ yields the requisite minimum value of zero when porosity is at a maximum. It is also noted that the mineralogy value $\alpha$ is empirical and lithology specific.

Since equation (1) shows the general form of curve $m_u$ to be as illustrated in FIG. 3, i.e. a logarithmic decline, $\alpha$ may be thought of as a value which determines the amount of concavity of the curve with respect to a straight line (not shown) connecting the end points of curve $m_u$. Therefore, one method is to use the computer 24 to iteratively process electrical signals potentially corresponding to $\phi_{max}$ and the paired value for $\sigma_{umin}$, $\sigma_{umax}$ and $\alpha$ to generate several potential second series of the form set forth in equation (1); graphically output (as indicated at 17) or otherwise illustrate these curves on a Cartesian graph of compressive strength versus porosity, along with points, such as 22, corresponding to the paired signals in the first series; and then choose that potential second series whose output curve can be seen visually to most nearly fit or lie near the upper periphery of the data cloud, again as shown in FIG. 3.

Figure 4:
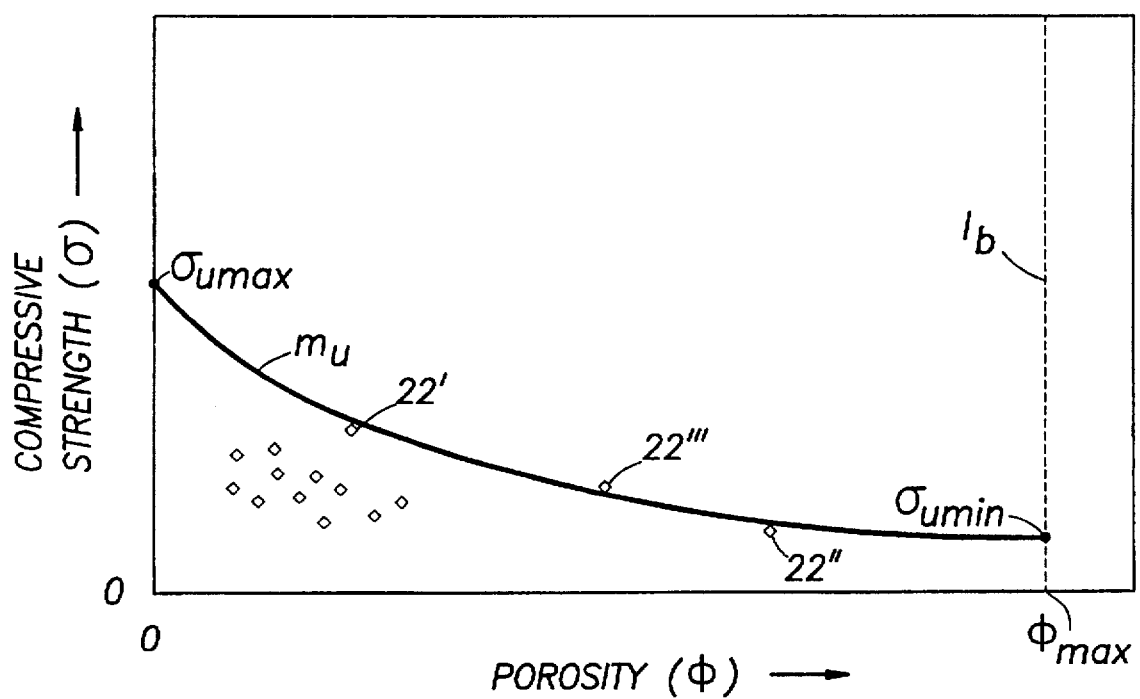
FIG. 4 is a graphical representation, similar to that of FIG. 3, illustrating proper curve fitting in an unusual example.

To further clarify what is meant by "fitting" the upper periphery of a data cloud, refer now to FIG. 4. It will be seen that the curve $m_u$' in FIG. 4, in taking the form of the known relationship, and then curve fitting as nearly as possible the upper periphery of the data cloud, actually only passes through two of the data points, specifically 22' and 22" and near a third 22'". This illustrates two important points. First, the concentration of most of the data points is well below the curve $m_u$', and in accord with conventional wisdom, the points 22', 22" and 22'" might well have been considered aberrations, and discarded from the data analyzed; and in any event, the curve would probably have been placed through the center of the overall data cloud, which would have given a drastically different result. However, experiments have indicated that $m_u'$ is in fact representative of the correct signal series for the data cloud depicted. Secondly, it is not necessary, and indeed is sometimes impossible, for the curve of the proper form, and having the best fit, to pass through all of the significant (upper fringe) data points. In this case, the curve does not pass precisely through point 22'", and in fact, passes below it, still representing the best fit for the upper periphery of the cloud in question, given the requisite form of a logarithmic decline.

The above-described method uses a combination of iterative processing of the signals mentioned, by the computer 24, coupled with human interaction, i.e. visually inspecting the various potential second series' curves with respect to the data cloud to pick the best fit. In other embodiments, it may be possible to program or configure the computer 24 to perform the entire "fitting" process.

In any event, by fitting the curve $m_u$ or $m_u'$ to the upper periphery of the data cloud, it is ensured that those samples which have been least damaged in collection and preparation are used to generate the relationship expressed in equation (1), and those more damaged are disregarded. Thus is the stress history of the samples taken into account to provide a more accurate assay of the unconfined compressive strength of rock of the lithology in question as it would occur in nature (virgin rock strength).

Referring again to FIG. 3, it can be seen that the data points 22 do not include any for which the porosity $\phi$ has a value of zero, and therefore, at which the compressive strength a is at a maximum. Likewise, there is no point 22 at which $\phi$ has a maximum value, and $\sigma$ has zero value, as described above. However, it is highly preferable for the processing described above to generate the series of curve $m_u$ so that it does extend to such maximum and minimum porosity values and the paired compressive strengths, $\sigma_{umax}$ and $\sigma_{umin}$ that the curve $m_u$, which will be used in modeling to be described below, will cover all possible cases.

Furthermore, it is important to bound the second series of signals, and the corresponding function as represented by curve $m_u$, by the aforementioned maximum porosity value, as indicated by line $l_b$. This ensures a more accurate model than if the curve $m_u$ were extended all the way down to meet the $\phi$ axis in FIG. 3. This is because, at the point at which the curve would meet the $\phi$ axis, one would assume a condition of zero compressive strength and a maximum porosity of one hundred (100%) percent. However, such conditions do not occur in nature. In fact, any rock occurring in nature would disintegrate, i.e. reach maximum porosity and minimum compressive strength, at a higher value for $\sigma$ and a lower value for $\phi$. Likewise, the reason effective solidity $S_e$ is defined as indicated above, rather than a more conventional definition of solidity as $1-\phi$, is for the convenience of causing $S_e$ to be zero at the true maximum porosity, again to more accurately reflect the way the rock behaves in nature.

Although, in less preferred embodiments, the second series of signals, corresponding to equation (1) and curve $m_u$, could be used to model, or at least "guesstimate," various conditions which must be evaluated in developing a well drilling plan, it is highly preferred that the relationship given in equation (1), and therefore the corresponding second series of signals, be adjusted for various conditions which affect the compressive strength of the rock. In other words, equation (1) and curve $m_u$ represent the behavior of the rock at standard conditions. Thus, electrical adjustment signals corresponding to values related to these condition(s) are generated and processed with the second series of signals to generate a cumulative series of electrical signals corresponding to adjusted compressive strength as a function not only of porosity, but also of those other condition(s).

The most important of the conditions for which such adjustment is preferably made is the effect of confining stress on the rock as it occurs in nature. To adjust equation (1) and the corresponding series of signals for confinement stress, the following protocol may be used:

A secondary plurality of rock samples, of essentially the same lithology as those of the first plurality, are collected and prepared as described above in connection with step box 16. As indicated in step box 26, similar compressive strength testing is performed on these secondary samples, an exemplary one of which is illustrated at 28, by applying compressive force in the axial direction until the sample fails at the compressive strength value $\sigma_1$, as indicated by the like-referenced arrows. However, in these tests, the samples are laterally confined with a confining stress $\sigma_3$, as indicated by the like-numbered vectors. For the present, the description will relate to a set of such tests all done at one given confining pressure $\sigma_3$, although as explained hereafter, the procedure would preferably be repeated for other sets of the secondary samples using different confining pressures. Of course, as with the tests on the primary rock samples, the porosity of each sample will have been determined prior to the compressive testing.

Accordingly, once again, a confined compressive strength $\sigma_1$ and a porosity $\phi$ are determined for each sample. A third series of pairs of electrical confined compressive strength and porosity signals are generated for processing in computer 24 as indicated by line 30. The signals of each such pair correspond, respectively, to the confined compressive strength and porosity for a respective one of the secondary samples, and these pairs of signals are graphically represented by the hollow data points 32 in FIG. 3. This third series of paired signals is processed by computer 24 to extrapolate additional such pairs of signals and generate a fourth series of electrical signals corresponding to confined compressive strength as a function of porosity, graphically illustrated by curve $m_c$. Again, such a curve may be one of the outputs 17 of computer 24.

Since the mineralogical value a will be constant for all rock samples of the lithology in question, whether tested confined or unconfined, and since $\alpha$ will already have been determined in developing the series of signals corresponding to curve $m_u$, a curve such as $m_c$ can be fitted to the upper periphery of the cloud of data points 32 without the need to iterate so many variables. Specifically, the curve $m_c$ and corresponding function and fourth series of signals may be viewed as an adjusted form of curve $m_u$ and its respective corresponding function and signal series, and may in fact be used as the aforementioned cumulative series if confinement stress is the only condition for which equation (1) is adjusted. In the present invention it has been found that this fourth series of signals, when viewed as an adjustment of the second series of signals, i.e. a cumulative series, will be of the form $$\sigma_c = S_e[\sigma_{umax} + \Delta\sigma_{max}(\sigma_3/\sigma_{3max})^\beta] + (1-S_e)[\sigma_{umin} + \Delta\sigma_{min}(\sigma_3/\sigma_{3max})^\beta] \quad (3)$$

where:

$\sigma_c$ = confined compressive strength $\sigma_3$ = confining stress $\sigma_{3max}$ = maximum laboratory confining stress applied during testing $\beta$ = a principal stress relationship value $\Delta\sigma_{max}$=maximum increase in rock strength at zero porosity and maximum confining stress ($\phi=0$, $\sigma_3=\sigma_{3max}$)

$\Delta\sigma_{min}$=minimum increase in rock strength at maximum porosity and maximum confining pressure ($\phi=\phi_{max}$, $\sigma_3=\sigma_{3max}$)

It is noted that the terms in equation (3) which represent changes, i.e. $\Delta\sigma_{max}$ and $\Delta\sigma_{min}$, refer to changes with respect to unconfined compressive strength for the same respective porosity values. Also, the expression ($\sigma_3/\sigma_{3max}$) could be adjusted to standard conditions for theoretical correctness, but this has been omitted here for simplicity, as the difference is negligible.

Although it is important for curve $m_c$ to be bounded by a maximum porosity (and corresponding minimum compressive strength) for purposes similar to those described in connection with curve $m_u$, in the exemplary embodiment just described, this will already have been done, since the maximum porosity for a given lithology is constant, and does not vary with confinement pressure or stress.

At this point, it is noted that, while we are still discussing the curve fitting process of a curve such as $m_c$ for a given set of the secondary samples tested at one confining pressure $\sigma_3$, other such sets of secondary samples will have been so tested, at different confining pressures, respectively, hence the presence of both terms $\sigma_3$ and $\sigma_{3max}$ in equation (3). $\sigma_{3max}$ corresponds to the highest such confining pressure used in these tests. (This assumes that $\sigma_{3max}$ for the testing process was chosen to be higher than any confining stress anticipated for in situ rock whose strength is to be modeled, but not excessively high; in less preferred embodiments, the term $\sigma_{3max}$ in equation (3) could be replaced by any given one of the confining pressures used in testing.)

Returning now to the procedure for curve fitting the upper periphery of a cloud of data points such as 32, where $\alpha$ is already known, it is simplest to begin with that cloud of data points, and corresponding signals, which result from the testing at $\sigma_{3max}$, and we assume point 32 to be from that set. For the time being, we set $\beta=1$. As mentioned, $\alpha$ (which is incorporated in $S_e$) is known, from the prior method steps described in connection with equation (1), and the form of curve $m_c$ is known to be given by equation (3). Therefore, to fit the curve $m_c$ to the upper periphery of the cloud of data points 32 resulting from testing at the maximum confining pressure $\sigma_{3max}$, one may simply iterate the terms $\Delta\sigma_{max}$ and $\Delta\sigma_{min}$ until a good curve fit is visually seen. Thus, while the form of curve $m_c$ may be produced as an output 17 from processing of the signals corresponding to points 32 with the signals corresponding to equation (1), the final curve fit, and determination of the final values for $\Delta\sigma_{max}$, $\Delta\sigma_{min}$, $\sigma_{cmax}$ (see FIG. 3), and $\sigma_{cmin}$ may best be done with human visual interaction. It is also helpful to note that, where, as postulated, curve $m_c$ fits the data cloud from the maximum test confining pressure, $\Delta\sigma_{max}$ may be visualized as the distance between points $\sigma_{umax}$ and $\sigma_{cmax}$ in FIG. 3, and likewise, the term $\Delta\sigma_{min}$ may be visualized as the distance between points $\sigma_{umin}$ and $\sigma_{cmin}$.

As previously mentioned, several sets of the secondary samples 28 will have been tested, each at a respective confining pressure $\sigma_3$. Up to this point, we have been discussing the generation of a fourth series of signals, corresponding to a curve of the form $m_c$, for just one of these sets of samples, i.e. that set which was tested at the maximum confining pressure. Now, consider that, for several such sets of tested samples, alternative such fourth series of signals will be generated in the manner described above, still leaving $\beta$, in equation (3), equal to one, and substituting for $\sigma_{3max}$ the actual confining pressure used in testing the respective set of secondary samples. This process will generate respective alternate fourth series of signals which correspond to curves (not shown) of accurate shape or form for the respective clouds of data points (not shown). However, unless the true value of $\beta$ happens to be equal to one for the lithology in question, these alternate curves will not lie along the upper peripheries of their respective clouds of data points. Therefore, we iterate different values for $\beta$ until these other curves do properly fit the upper peripheries of their data clouds. This yields a final actual value for $\beta$, whereby equation (3) may be made generic to all possible confinement stresses and becomes the equation corresponding to the cumulative series of signals if confinement stress is the only condition for which the series corresponding to equation (1) is adjusted.

In the exemplary embodiment just defined, all the steps dealing with the data gathered at step box 26 and the corresponding signals may be considered part of the generation of the generic equation (3), and thus of the generation of the cumulative series (even if additional adjustment factors are added, as described below); and the electrical signals corresponding to data points such as 32 (third series), curves such as $m_c$ (fourth series), and/or value $\beta$ may be considered "stress adjustment signals" for purposes of the present invention.

In other embodiments, other processes may be used to adjust for confinement stress in producing the cumulative series. For example, instead of working directly with equation (3) and corresponding series of electrical signals, it is possible to perform a similar process using the following equation:

$$\Delta\sigma_c=[S_e\Delta\sigma_{max}+(1-S_e)\Delta\sigma_{min}](\sigma_3/\sigma_{3max})^\beta \quad (4)$$

where:

$\Delta\sigma_c$=the change in rock strength due to confining stress and then further process the resulting signals by performing the electronic equivalent of adding $\Delta\sigma_c$ from equation (4) to $\sigma_u$ from equation (1) to yield the cumulative series.

In less preferred embodiments, one might test only a single set of samples 28 at one confining pressure $\sigma_3$, generate a curve such as $m_c$ by working with the data points 32 and their corresponding signals in the same manner as described above for the generation of the curve $m_u$, and then simply use the signal series corresponding to that single curve of the form $m_c$ as the cumulative series. Indeed, in these less preferred embodiments, this may be done without ever performing any of the unconfined stress tests 16 and related processing steps. However, it should be understood that modeling from such a series would have similar drawbacks to modeling from the series represented by equation (1) and curve $m_u$, in that the model would only be truly valid or completely accurate for one confinement condition.

Preferably, equation (3) and the corresponding series of electrical signals are further adjusted to account for changes in compressive strength due to a dip angle of a bedding plane of the rock. The effect of orientation on rock strength can be significant for highly laminated rocks such as shale. For instance, a maximum reduction in shale strength of about 40% has been observed at a critical relative dip angle of about 55°. This critical angle occurs when bedding planes coincide with the internal plane f of greatest shear stress (see box 16). Thus, additional electrical adjustment signals are generated as orientation adjustment signals corresponding to such changes.

A tertiary plurality of samples 36 of similar lithology to that involved thus far, but having strata or bedding planes 38 lying at an oblique angle to the central axes of the cylindrical samples are used.

Several sets of such samples are tested, under unconfined conditions as shown in step box 34, with the samples of each set having a constant porosity $\phi$ but differing as to bed plane angle $\theta$. Corresponding compressive strength, porosity, and bed plane angle signals are generated for processing by computer 24, as indicated by line 35.

Figure 5:
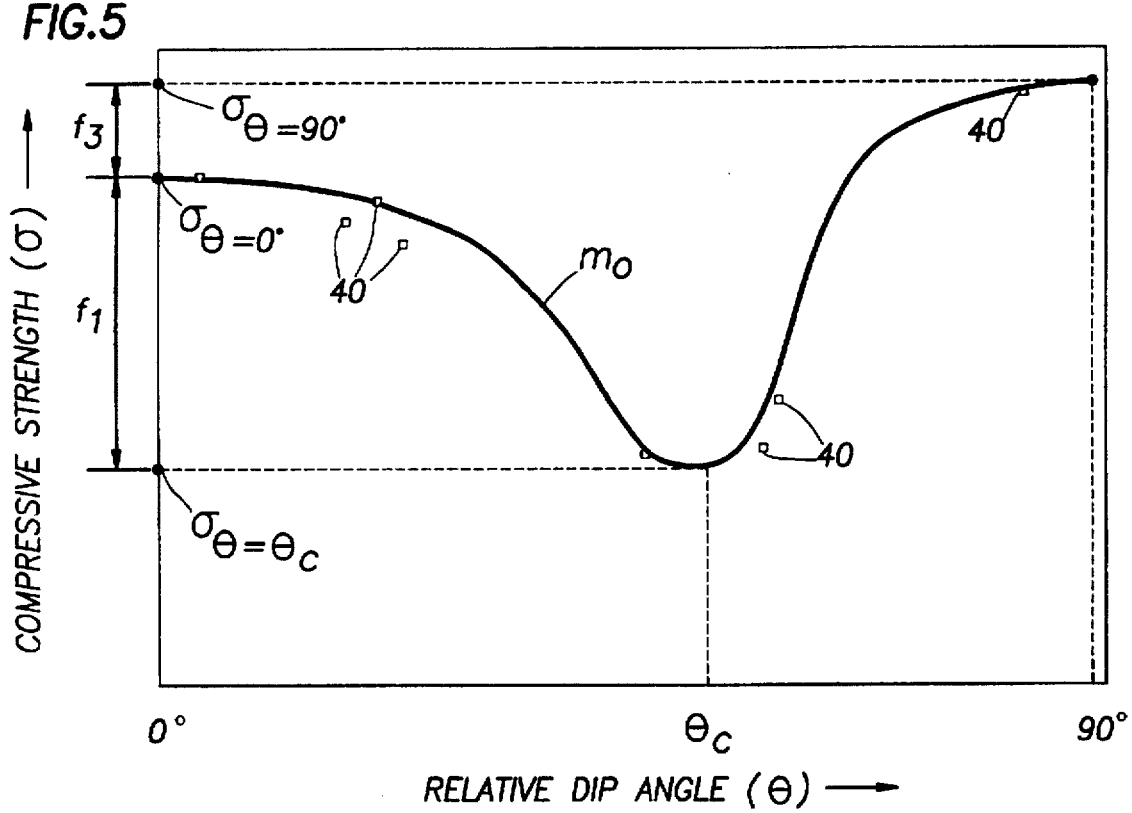
FIG. 5 is a graphical representation corresponding to the development of adjustment signals for relative dip angle, for rock of relatively low porosity.

FIG. 5 graphically depicts the manner in which compressive strength varies with relative dip angle $\theta$ for one given porosity $\phi$. (For purposes of this application, "relative dip angle" will mean dip angle with respect to the borehole axis rather than with respect to earth. If the relative dip angle $\theta$ is 0°, the bedding planes are perpendicular to the borehole axis; if the relative dip angle $\theta$ is 90°, the bedding planes are parallel to the borehole axis.) In the present invention it has been discovered that the $\theta/\sigma$ relationship is represented by a curve of the form of $m_o$ and that curve will generally correspond to an equation of the form:

$$\sigma_{co} = S_e[\sigma_{umax} + \Delta\sigma_{max}(\sigma_3/\sigma_{3max})^\beta](1-c_{omax}) + (1-S_e)[\sigma_{umin} + \Delta\sigma_{min}(\sigma_3/\sigma_{3max})^\beta](1-c_{omin}) \quad (5)$$

where:
for $0<\theta \leq \theta_c$:

$$\gamma = (\theta/\theta_c)\pi/2 \quad (6)$$

$$f_1 = (\sigma_{\theta=0} - \sigma_{\theta=\theta_c})/\sigma_{\theta=0}, \text{ at zero porosity} \quad (7)$$

$$f_2 = f_1, \text{ at maximum porosity} \quad (8)$$

$$c_{omax} = f_1 \sin^n(\gamma) \quad (9)$$

$$c_{omin} = f_2 \sin^n(\gamma) \quad (10)$$

, and for $\theta_c < \theta \leq 90°$:

$$\gamma = \pi/2 + (\theta - \theta_c)/(1 - \theta_c 2/\pi) \quad (11)$$

$$f_3 = (\sigma_{\theta=90°} - \sigma_{\theta=0})/\sigma_{\theta=0}, \text{ at zero porosity} \quad (12)$$

$$f_4 = f_3 \text{ at maximum porosity} \quad (13)$$

$$c_{omax} = (f_1 + f_3) \sin^n(\gamma) - f_3 \quad (14)$$

$$c_{omin} = (f_2 + f_4) \sin^n(\gamma) - f_4 \quad (15)$$

and:

$\sigma_{co}$=compressive strength adjusted for confinement stress and orientation $c_{omax}$=maximum orientation correction at zero porosity $c_{omin}$=minimum orientation correction at maximum porosity $f_1$=maximum percent reduction in compressive strength at critical relative dip angle ($\theta=\theta_c$ as compared to $\theta=0°$), at zero porosity $f_2$=maximum percent reduction in compressive strength at critical relative dip angle ($\theta=\theta_c$ as compared to $\theta=0°$), at maximum porosity $f_3$=maximum percent increase in compressive strength parallel to dip angle ($\theta=90°$ as compared to $\theta=0°$), at zero porosity $f_4$=maximum percent increase in compressive strength parallel to dip angle ($\theta=90°$ as compared to $\theta=0°$), at maximum porosity $\theta$=relative dip angle of bedding planes with respect to the wellbore axis.

$\theta_c$=critical relative dip angle where compressive strength reaches a minimum value.

$\gamma$=sine function parameter derived from relative dip angle that reaches a maximum value of $\pi/2$ when $\theta=\theta_c$ $\sigma_\theta$=compressive strength at a specific relative dip angle $\theta$ n=an orientation exponent For one of the sets of tertiary samples, a series of pairs of electrical signals, the signals of each pair corresponding, respectively, to the relative dip angle $\theta$ and compressive strength a for a given sample, are generated, and these may be outputted at 17, and in any event visualized, as data points such as 40 in FIG. 5. Knowing the general form of equation (5) as well as the general form of its representation as a curve such as $m_o$ (a conjunction of portions of two different sine waves), one can then fit a curve $m_o$ and a corresponding series of signals (generated by processing the signals corresponding to points 40) to the upper periphery of the cloud of data points 40 by iterating estimated values for $\theta_c$, $f_1$, $f_2$, $f_3$, $f_4$, and n, either by further processing of the signals and/or by at least some human visual intervention referring to a graphical representation such as shown in FIG. 5. As in other contexts above, fitting the upper periphery of the cloud takes stress history into account.

Figure 6:
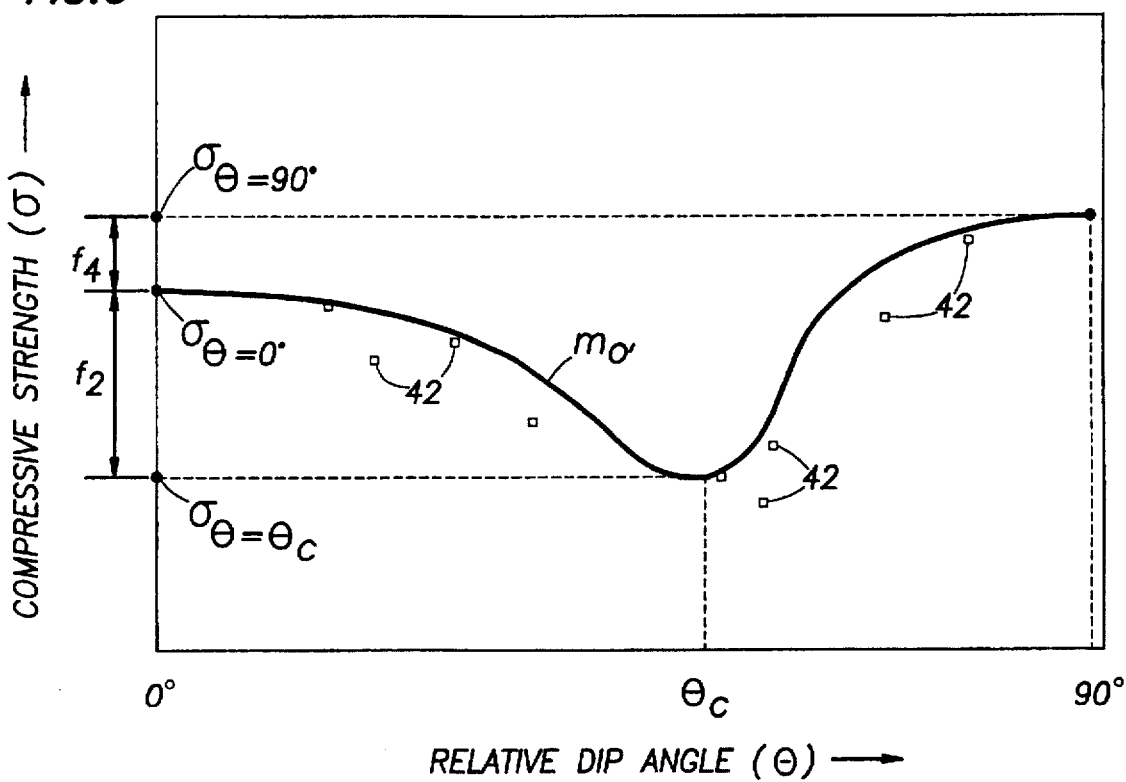
FIG. 6 is a graphical representation, similar to that of FIG. 5, for rock of relatively high porosity.

Preferably, if only two sets of samples have been tested, the porosities of the two sets, respectively, are near zero (which is the case illustrated in FIG. 5), and near maximum porosity (which is the case illustrated in FIG. 6). In FIG. 6, the data points corresponding to the relative dip angles $\theta$ and compressive strengths $\sigma$, and the corresponding signals, for the second set are indicated at 42, and the curve fitted to the upper periphery of this cloud of data points in FIG. 6 is labeled $m_o'$.

Once at least two such curves have been fitted, and final values determined for the variables iterated in order to fit those curves, it is then possible to determine values for $c_{omax}$ and $c_{omin}$, and generate corresponding signals, which are the unknowns ultimately needed to solve equation (5). Thus, the signals corresponding to $c_{omax}$ and $c_{omin}$ are the ultimate orientation adjustment signals, and equation (5) now corresponds to the cumulative series of signals, if confinement stress and orientation are the only factors for which adjustment is made. Conceptually, $c_{omax}$ and $c_{omin}$ may be viewed as factors which adjust the curve $m_c$ (FIG. 3) by moving its end points vertically, with the term $S_e$ resulting in proper translation of all intermediate points, to result in a curve corresponding to the cumulative series of equation (5).

As mentioned, in the exemplary embodiment, the only tests done at step box 34 are done in unconfined condition. However, in more detailed embodiments, it would be possible to develop additional data by repeating the process described above for other sets of tertiary samples tested at one or more confining pressures (compare step box 26).

As before, there are other equivalent ways of processing. For example, the following equation corresponds to a combination correction signal for compressive stress and orientation, which could simply be added to equation (1) to produce the cumulative equation, and of course, the computer 24 could perform the electronic equivalent by processing the signals corresponding to equations (7) and (1) to produce the cumulative series, (if compressive stress and orientation are the only factors for which correction or adjustment is made):

$$\Delta\sigma_{co} = S_e[\sigma_{umax} + \Delta\sigma_{max}(\sigma_3/\sigma_{3max})^\beta](-c_{omax}) + (1-S_e)[\sigma_{umin} + \Delta\sigma_{min}(\sigma_3/\sigma_{3max})^\beta](-c_{omin}) \quad (16)$$

In the most highly preferred embodiments, it is also preferable to further adjust for changes in compressive strength due to temperature, and in the present invention it has been found that such temperature effects are functionally related to confinement pressure. The effect of temperature on compressive strength is ordinarily relatively low, e.g. on the order of 2-7%, for most, but not all, lithologies, in the temperature range of interest. Therefore, for some lithologies, the effect could be more significant. Furthermore, at high confining pressures, the temperature effect becomes more pronounced, and therefore more significant.

Because of the discovered relationship of confinement stress on temperature, a greater number of subsets of quaternary samples are preferably tested in the operation indicated by step box 44.

In the present invention it has been found that the fully adjusted cumulative series, i.e. adjusted for confinement stress effects, orientation effects, and temperature effects, will be of the form:

$$\sigma_{cof} = S_e [\sigma_{smax} + \Delta\sigma_{max}(\sigma_3/\sigma_{3max})^\beta](1-C_{omax})(1-c_{tmax}) + (1-S_e) \\ [\sigma_{smin} + \Delta\sigma_{min}(\sigma_3/\sigma_{3max})^\beta](1-c_{omin})(1-c_{tmin}) \quad (17)$$

where:

$$c_{tmin} = [(T-T_s)/(T_{max}-T_s)]^b [(\sigma_3/\sigma_{3max})^a (f_5-f_6)+f_6] \quad (18)$$

$$c_{tmax} = [(T-T_s)/(T_{max}-T_s)]^b [(\sigma_3/\sigma_{3max})^a (f_7-f_8)+f_8] \quad (19)$$

$f_5$=percent reduction in compressive strength at maximum test temperature and maximum test confining stress ($T=T_{max}$, $\sigma_3=\sigma_{3max}$) at maximum porosity ($\phi=\phi_{max}$).

$f_6$=percent reduction in compressive strength at maximum test temperature and standard pressure ($T=T_{max}$, $\sigma_3=0$), at maximum porosity ($\phi=\phi_{max}$).

$f_7$=percent reduction in compressive strength at maximum test temperature and maximum test confinement stress ($T=T_{max}$, $\sigma_3=\sigma_{3max}$), at zero porosity ($\phi=0$).

$f_8$=percent reduction in compressive strength at maximum test temperature and standard pressure ($T=T_{max}$, $\sigma_3=0$), at zero porosity ($\phi=0$).

$\sigma_{cof}$=compressive strength adjusted for confinement stress, orientation, and temperature.

$T_{max}$=maximum test temperature.

$T_s$=standard temperature.

$T$=temperature.

$a$=a pressure-strength relationship value.

$b$=a temperature-strength relationship value.

The process indicated in step box 44 would preferably involve the testing of at least eighteen (18) sets of quaternary samples. A first family of those sets will all have a common porosity in the samples, and that porosity is preferably as low as possible $\phi_L$. This family preferably includes three sets of quaternary samples, one of which is tested unconfined, a second of which is tested at a first confinement stress, and the third of which is tested at another confinement stress, greater than the first confinement stress and equal to $\sigma_{3max}$ (step box 26). Each of these sets, in turn, preferably includes at least three sub-sets, each of which is tested at a different temperature (although in less preferred embodiments, it may be possible to work with only two such sub-sets per set). The second family includes quaternary samples all having a common, relatively high, porosity $\phi_h$, and having sets and sub-sets otherwise corresponding to those of the first family.

Figure 7:
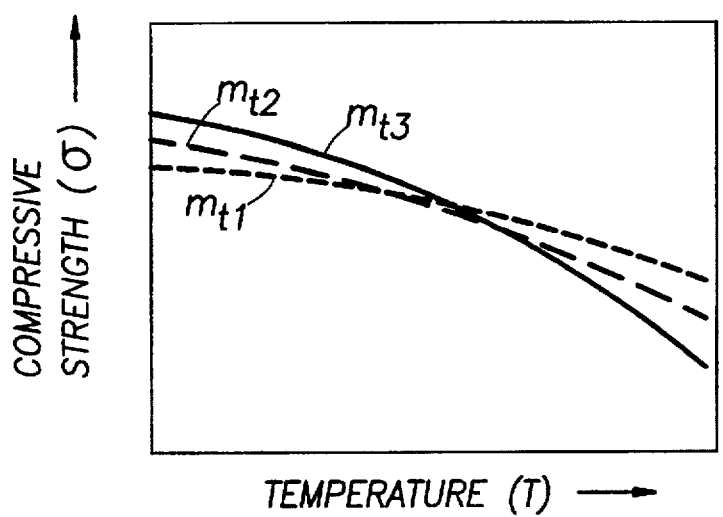
FIG. 7 is a graphical representation, similar to that of FIG. 5, illustrating the generation of adjustment signals for temperature, for rock of relatively low porosity.

FIG. 7 graphically depicts an upper periphery curve fit for the test results from such a first family. Thus, the porosity $\phi_L$ for all points on the curves $m_{T1}$, $m_{T2}$, and $m_{T3}$ is the same and is relatively low. Curve $m_{T1}$ reflects the way compressive strength $\sigma$ varies with temperature T without any confinement stress; curve $m_{T2}$ shows such variation with a first (lower) confinement stress; and curve $m_{T3}$ represents such variation where the samples are confined at the highest confinement stress used in the series of tests. Thus, each of the curves in FIG. 7 depicts one of the aforementioned sub-sets of tests, so that only temperature and compressive strength vary, as porosity and confinement stress is constant for each sub-set.

Accordingly, the tests from which these three curves would be developed would produce, for each such sub-set, a temperature T and compressive strength $\sigma$ for each sample. Based on these, a respective set of paired electrical signals, the signals of each pair corresponding, respectively, to the temperature T and compressive strength $\sigma$ for a given sample in the respective sub-set, would have been generated, and corresponding data points could have been graphically depicted in FIG. 7 (not shown). These signals, for each sub-set of quaternary samples respectively, would be processed by computer 24 to extrapolate additional such pairs and generate a series of signals corresponding to the respective curve, and as described in other contexts above, each curve would be fitted to the upper periphery of the respective cloud of data points by iterating estimated values for $f_5$, $f_6$, $f_7$, $f_8$, a, and b.

As with orientation, the reason it is preferred that the porosity for all the tests represented by FIG. 7 be relatively low is so that the extrapolations performed by computer 24 in generating series of signals corresponding to equations (17), (18) and/or (19) will be as accurate as possible for zero porosity (since it is virtually impossible to obtain samples with zero porosity). The same applies for the relatively high porosity for the second family of quaternary samples vis a vis the impossibility of obtaining samples with maximum porosity.

Figure 8:
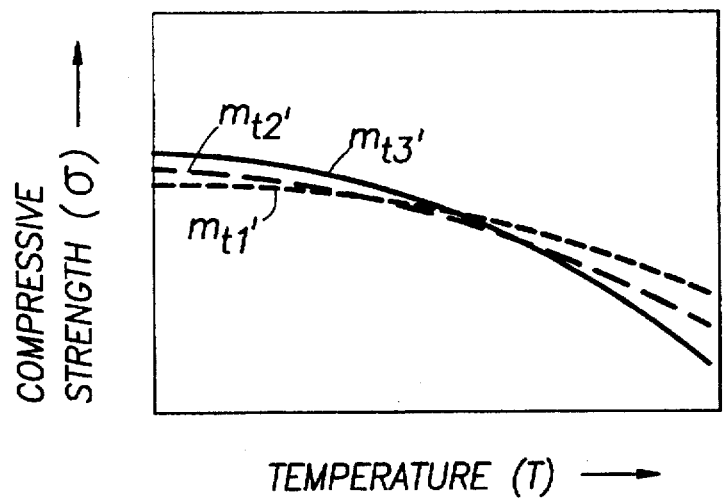
FIG. 8 is a graphical representation, similar to that of FIG. 7, for rock of relatively high porosity.

As just implied, FIG. 8 graphically depicts the same type of information as FIG. 7, but for the second family of quaternary samples, having relatively high porosity.

Once the two families of curves depicted in FIGS. 7 and 8 have been fitted (at least two curves per $\phi$ value), and final values determined for $f_5$, $f_6$, $f_7$, $f_8$, a and b, it is then possible to determine values for $c_{tmin}$ and $c_{tmax}$, using equations (18) and (19), and generate corresponding signals, which are the unknowns ultimately needed to solve equation (17). Thus, the signals corresponding to $c_{tmin}$ and $c_{tmax}$ in this embodiment, are the ultimate temperature adjustment signals, and equation (17), as mentioned, corresponds to the ultimate cumulative series of signals. Like $c_{omax}$ and $c_{omin}$, $c_{tmax}$ and $c_{tmin}$ may be viewed as factors which adjust the curve $c_c$ (FIG. 3) by indicating the vertical adjustment at the end points, with the term $S_e$ then resulting in proper translation of all intermediate points.

The signals corresponding to the T and $\sigma$ values exemplified in FIGS. 7 and 8 may, for this embodiment, be viewed as temperature variable signals; $f_5$, $f_6$, $f_7$, $f_8$, a and b may be viewed as intermediate temperature signals; and $c_{tmin}$ and $c_{tmax}$ may be viewed as the ultimate temperature adjustment signals which correspond, respectively, to a minimum temperature adjustment value (at maximum porosity) and a maximum temperature adjustment value (at minimum porosity).

Note that equations (17), (18) and (19) are good if tests at 44 have been performed at a confining stress equal to $\sigma_{3max}$ (equation (3)) and at least one lower confining stress. Otherwise, equations (17), (18) and (19) would have to be modified to include different terms for the respective maximum confining stresses used at steps 26 and 44.

In another embodiment, a signal series which may be added to the series corresponding to equation 1 to result in a cumulative series adjusted for compressive stress, orientation, and temperature, corresponds to the equation:

$$\Delta\sigma_{cor}=S_e[\sigma_{omax}+\Delta\sigma_{max}(\sigma_3/\sigma_{3max})^\beta](1-c_{omax})(-c_{tmax})+(1-S_e)$$
$$[\sigma_{omin}+\Delta\sigma_{min}(\sigma_3/\sigma_{3max})^\beta](1-c_{omin})('1c_{tmin}) \quad (20)$$

In still other embodiments, it is possible to develop individual adjustment signals for each of the conditions for which adjustment is made, independently of one another, and add all of those to equation (1). In this case, in preferred embodiments, one or more of the individual adjustment signals may be developed as a function of one or more of the other conditions; for example, a temperature adjustment signal, which does not also adjust for confinement stress, may nevertheless be developed as a function of confinement stress. Furthermore, in less preferred embodiments, only some of these individual adjustment signals may be added to the first series of signals if it is not desired to adjust for all of the aforementioned conditions.

In any event, having arrived at some cumulative series, depending upon the conditions for which adjustment is desired, and thus at a general assay of compressive strength as a function (at least) of porosity for one relatively pure lithology, e.g. sandstone, the entire process is preferably repeated to provide an assay for relatively pure shale, a significantly different lithology, or any other lithology(ies) anticipated along locus 1. One or both of these assays is then used in modeling the compressive strength at least at several sites along the locus 1 of well bore 14, and preferably, to provide a continuous model for all such sites.

More specifically, site characteristics of the rock for the locus 1 are determined at a plurality of sites along the length of the locus, and as the rock would be addressed by a drill bit. These site characteristics include porosity and other physical properties similar to those used to generate any adjustment signals incorporated in the cumulative series. In addition, the site characteristics for each site should include values corresponding to the relative percentages of the lithologies (in this case sandstone and shale) for each site. This may be done in advance of drilling well bore 12 using logs and other relevant data, diagrammatically indicated at 50, from a nearby well bore 52 which has been drilled through rock which is presumptively the same or similar to that along locus 1.

Site signals, corresponding to the respective site characteristics, are generated and processed by computer 24 with the cumulative series to generate in situ compressive strengths corresponding to the in situ compressive strengths of the rock at each site. More specifically, the computer performs the electronic equivalent of substituting the values for site characteristics for the corresponding variables in the equation for the cumulative series, and then solving.

If the site characteristics indicate that at least a portion of locus 1 passes through rock of mixed lithology, the site characteristics (other than percentages of sandstone and shale) are used to generate two compressive strength signals for that site, one from the cumulative series based on sandstone, and the other from the cumulative series based on shale. Then, computer 24 processes those signals to take a weighted average based on the aforementioned percentages. Other aspects of preferred embodiments of the invention pertain to the manner in which the various site signals are generated. Some site characteristics and corresponding signals may relate to local conditions (e.g. overburden, overbalance, geological stress) other than those corresponding to the variables in the cumulative series and may be used to further refine the model.

Relative dip angle data may be available directly from MWD or well logs. Relative dip may also be calculated if directional survey data and formation dip and azimuth data are available. A preferred method for electronically calculating it, i.e. generating a signal corresponding to the relative dip angle at a given site along locus 1, will now be described. For each site, an electrical wellbore angle signal corresponding to the well bore inclination angle, an electrical well bore azimuth signal corresponding to the well bore azimuth, an electrical bed plane angle signal corresponding to the dip angle of the bed plane with respect to the earth, and an electrical bed plane dip azimuth signal corresponding to "dip azimuth" (i.e. the compass or azimuthal direction in which the bed plane dips) are generated. These signals are processed to generate an electrical relative dip angle signal corresponding to the relative dip angle $\theta$ of the bed plane with respect to the borehole at the respective site by performing the electronic equivalent of using a vector dot product, as follows:

$$\cos\theta = i_d i_w + j_d j_w + k_d k_w \quad (21)$$

where $(i_d, j_d, k_d)$ and $(i_w, j_w, k_w)$ are unit vectors $u_d$ and $u_w$ describing the direction of lines normal to the formation dip plane, and parallel to the wellbore axis, respectively. The relative dip angle should be constrained to be less than 90°, or using computer logic:

$$\text{If } \theta > \pi/2 \text{ then: } \theta = \pi - \theta \quad (22)$$

The i,j,k components of the unit vector $u_d$ describing a line normal to the dipping formation plane may be expressed as:

$$i_d = \sin\lambda_d \sin(A_d - \pi) \quad (23)$$

$$j_d = \sin\lambda_d \cos(A_d \pi) \quad (24)$$

$$k_d = \cos\lambda_d \quad (25)$$

The i,j,k components of the unit vector $u_w$ describing a line parallel to the wellbore axis may be expressed as:

$$i_w = \sin\lambda_w \sin A_w \quad (26)$$

$$j_w = \sin\lambda_w \cos A_w \quad (27)$$

$$k_w = \cos\lambda_w \quad (28)$$

where:

$\lambda_d$ = formation dip angle $A_d$ = formation dip azimuth $\lambda_w$ = wellbore inclination angle $A_w$ = wellbore azimuth For any of the site signals corresponding to confinement stress, in generating the corresponding site signal, greater accuracy is achieved if one or more of several local physical conditions are taken into account. These are: the pressure differential between fluid in the well bore and fluid in the surrounding formation ("overbalance"), the effective stress due to overburden, and the effective stress due to the local geological stress field.

In general terms, the confining stress $\sigma_3$ may be expressed as a function of the effective stress due to overbalance, the effective stress due to overburden, and the effective stress due to the local geologic stress field expressed as a resultant vector.

The effective confining stress due to overbalance at a given depth may be expressed as:

$$\sigma_b = \sigma_{md} + \sigma_{jf} + \sigma_{pof} - \sigma_{pore} \quad (29)$$

where:

$\sigma_b$=effective stress due to overbalance $\sigma_{md}$=pressure exerted on bottom due to the dynamic mud weight (i.e. includes the incremental increase in static mud weight due to annular friction losses)

$\sigma_{jf}$=pressure exerted on bottom due to jet impact force $\sigma_{pof}$=pump-off stress due to the constricted annular area between the bit and the wellbore $\sigma_{pore}$=formation pore pressure. Note that if the formation permeability is essentially zero (or negligible) then the effective pore pressure is zero.

The effective stress due to overburden $\sigma_x$ has different horizontal and vertical components. In one preferred embodiment of the present invention, we consider forces acting at a point on an annulus of rock perpendicular to the wellbore at a given site of interest.

The horizontal confinement stress due to overburden acts radially at such a point at any vertical depth and is uniform in all horizontal directions. It may be represented as the vector $\sigma_h u_h$ where $\sigma_h$ is the magnitude of horizontal stresses due to overburden, and $u_h$ is a unit vector describing the direction of $\sigma_h$ at the point of interest. Note that the direction of $u_h$ is defined by any azimuth. The magnitude of $\sigma_h$ may be estimated as:

$$\sigma_h = \sigma_{fp} - \sigma_{pore} \quad (30)$$

where:

$\sigma_{fp}$=fracture propagation pressure $\sigma_{pore}$=formation pore pressure Other methods to determine the magnitude of $\sigma_h$ are disclosed in prior art, such as U.S. Pat. No. 4,981,037. $u_h$ has the following vector components:

$$i_h = \sin A = i \text{ of interest} \quad (31)$$

$$j_h = \cos A = j \text{ of interest} \quad (32)$$

$$k_h = 0 \quad (33)$$

where:

A=azimuth of interest

The vertical confinement stress due to overburden acts vertically downwardly by at any vertical depth, and may be expressed as $\sigma_v u_v$ where $u_v$ is a unit vector describing the direction of $\sigma_v$. Methods to estimate the magnitude of $\sigma_v$ are disclosed in prior art such as U.S. Pat. No. 4,981,037. $u_v$ has the following vector components:

$$i_v = 0 \quad (34)$$

$$j_v = 0 \quad (35)$$

$$k_v = 1 \quad (36)$$

The confinement stress due to local geologic stress field may be expressed as $\sigma_g u_g$ where $u_g$ is a unit vector describing the direction of $\sigma_g$. The magnitude of $\sigma_g$ may be measured or partially inferred from structural features. $u_g$ has the following vector components:

$$i_g = \sin \lambda_g \sin A_g \quad (37)$$

$$j_g = \sin \lambda_g \cos A_g \quad (38)$$

$$k_g = \cos \lambda_g \quad (39)$$

where:

$A_g$=azimuth of local geologic stress field $\lambda_g$=inclination of local geologic stress field In order to apply the vectors $\sigma_h u_h$, $\sigma_g u_g$, and $\sigma_v u_v$, we must define the aforementioned point of interest on the aforementioned annulus of rock at the site in question. This in turn requires that we determine unit vectors in the directions of circumferential, axial, and lateral forces applied by the bit at the point of interest with respect to the wellbore (and bit) axis.

For this purpose, we define an angle $\eta$. $\eta$ is defined as any arbitrary angle referenced from the high side of the hole (positive clockwise) and lies in the plane of the aforementioned rock annulus. $\eta_d$ is defined as the acute angle from high side to the point along the circumference of the wellbore where the torsional bit force is parallel to dip. It is necessary to define $\eta_d$ in order to precisely define the relative dip angle for the point of interest.

Recall the definitions of $\theta$, $u_d$, and $u_w$ in equations 21, 23 through 25, and 26 through 28, respectively.

Next we define $v_1$ which is the projection of $u_d$ in the direction of $u_w$:

$$v_1 = u_w \cos \theta \quad (40)$$

$$i_1 = i_w \cos \theta \quad (41)$$

$$j_1 = j_w \cos \theta \quad (42)$$

$$k_1 = k_w \cos \theta \quad (43)$$

Next we define $v_2$ which is the vector from the tip of $u_d$ to the tip of $v_1$. Vector $v_2$ is orthogonal to $u_w$, and points towards the dipping formation. This vector and the high side vector described below subtend the angle $\eta_d$.

$$v_2 = v_1 - u_d \quad (44)$$

$$i_2 = i_1 - i_d \quad (45)$$

$$j_2 = j_1 - j_d \quad (46)$$

$$k_2 = k_1 - k_d \quad (47)$$

Converting $v_2$ to a unit vector $u_2$ in the same direction as $v_2$ we have:

$$u_2 = v_2 / |v_2| \quad (48)$$

Next we define a high side vector $u_{hs}$, a unit vector pointing to the high side of the wellbore in the plane of the rock annulus as follows:

$$i_{hs} = \sin(\lambda_w + \pi/2) \sin A_w \quad (49)$$

$$j_{hs} = \sin(\lambda_w + \pi/2) \cos A_w \quad (50)$$

$$k_{hs} = \cos(\lambda_w + \pi/2) \quad (51)$$

Finally the angle $\eta_d$ may be determined from the following vector dot product:

$$\cos \eta_d = u_2 \cdot u_{hs} = i_2 i_{hs} + j_2 j_{hs} + k_2 k_{hs} \quad (52)$$

Since $\eta_d$ has a valid range of $-\pi/2 \leq \eta_d \leq \pi/2$, $\eta_d$ should be constrained within this range, or using computer logic:

$$\eta_d > \pi/2 \text{ then: } \eta_d = \eta_d - \pi \quad (53)$$

Now, having defined, mathematically (and thus also in corresponding electric signals) the aforementioned point of interest on the rock annulus, we can proceed to calculate (process signals) to determine the compressive strength signal at that point. In the preferred embodiment, this is done by breaking down the total compressive strength into those components which oppose circumferential (torsional), axial and lateral bit force, respectively. In mathematical terms:

The total in-situ rock strength opposing the total drilling force may be expressed as:

$$\sigma_i = f_i \sigma_{1t} + f_a \sigma_{1a} + f_l \sigma_{1l} \quad (54)$$

and, $$1 = f_t + f_a + f_l \quad (55)$$

where:

$\sigma_i$=in-situ rock strength opposing the total bit force
$f_t$=torsional fraction of the total bit force (applied force)
$\sigma_{1t}$=in-situ rock strength opposing the circumferential bit force
$f_a$=axial fraction of the total bit force (applied force)
$\sigma_{1a}$=in-situ rock strength opposing the axial bit force
$f_l$=lateral fraction of the total bit force (reactive force, zero mean value, negligible with BHA stabilization)
$\sigma_{1l}$=in-situ rock strength opposing the lateral bit force To define the compressive strength opposing the torsional (circumferential) bit force at any point on the rock, we first obtain unit vectors describing the directions of $\sigma_{1t}$, $\sigma_{2t}$, and $\sigma_{3t}$, at the point of interest. ($\sigma_{2t}$ is confining stress perpendicular to $\sigma_{1t}$ and $\sigma_{3t}$.) Any point of interest may be defined by a respective arbitrary value of angle $\eta$.

For a given value of angle $\eta$, we define a unit vector perpendicular to the wellbore axis pointing in the direction defined by angle $\eta$. To precisely define the unit vector, we obtain its inclination and azimuth angles as follows:

$$\tan A_3 = \tan \eta / \cos \lambda_w \quad (56)$$

where:

$A_3$=azimuth difference between $u_3$ and $u_w$
Note that if $\lambda_w = \pi/2$, then $A_3 = \pi/2$ $$A_r = A_w + A_3 + \pi \quad (57)$$

and $$\cos \lambda_r = \cos \eta \sin \lambda_w \quad (58)$$

where:

$A_r$=azimuth of unit vector $u_3$
$\lambda_r$=inclination angle of unit vector $u_3$ Next we define $u_3$ a unit vector orthogonal to both the wellbore axis and to $\sigma_{1t}$, as follows:

$$i_3 = \sin \lambda_r \sin A_r \quad (59)$$

$$j_3 = \sin \lambda_r \cos A_r \quad (60)$$

$$k_3 = \cos \lambda_r \quad (61)$$

Finally, a unit vector $u_{\sigma a t}$ describing the direction of $\sigma_{1t}$, the rock strength opposing the circumferential bit force, at the point of interest may be determined from the following vector cross product (the cross product follows the "left-hand" rule since the vertical axis is positive downwards):

$$u_{\sigma 1t} = u_3 \times u_w \quad (62)$$

$$i_{\sigma 1t} = j_3 k_w - k_3 j_w \quad (63)$$

$$j_{\sigma 1t} = k_3 i_w - i_3 k_w \quad (64)$$

$$k_{\sigma 1t} = i_3 j_w - j_3 i_w \quad (65)$$

Unit vectors $u_{\sigma 2t}$ and $u_{\sigma 3t}$ describing the directions of $\sigma_{2t}$ and $\sigma_{3t}$, the orthogonal confinement stresses accompanying the circumferential bit force, at the point of interest have already been determined above and are defined as follows:

$$u_{\sigma 2t} = u_3 \quad (66)$$

$$u_{\sigma 3t} = -u_w \quad (67)$$

The confinement stress at the point of interest may be obtained by projecting all confinement stresses in the directions defined by $u_{\sigma 2t}$ and $u_{\sigma 3t}$, and then summing all of the scalar components in each direction. The confinement stress is then the lesser of these two vectorial stress summations, since the confinement stress is always defined by the minimum principal stress. One of these confinement stresses $\sigma_{2t}$ may be determined as follows:

$$\sigma_{2t} = |(\sigma_h \mu_h + \sigma_v \mu_v + \sigma_g \mu_g) \cdot u_{\sigma 2t}| \quad (68)$$

In eq. (68) note that $u_h$ acts in the direction of $u_{\sigma 2t}$ (i.e. $u_h$ has the same i and j components as $u_{\sigma 2t}$). The absolute value of each component is summed as the summation is bidirectional.

The other orthogonal confinement stress $\sigma_{3t}$ is:

$$\sigma_{3t} = \sigma_b - (\sigma_h \mu_h + \sigma_v \mu_v + \sigma_g \mu_g) \cdot u_{\sigma 3t} \quad (69)$$

In eq. (69) note that $u_h$ acts in the direction of $u_{\sigma 3t}$ (i.e. $u_h$ has the same i and j components as $u_{\sigma 3t}$). The matrix stresses are subtracted from the overbalance. Note that only the positive components of the vector projections are summed in the direction of $u_{\sigma 3t}$ because the negative components are replaced by the fluid pressure term $\sigma_b$ (i.e. all negative components are discarded). If $\sigma_{2t}$ is less than $\sigma_{3t}$ then lost circulation is likely to occur.

The in-situ rock compressive strength is then computed using the minimum confinement stress just determined above and the relative dip angle defined by angle $\eta$. The relative dip angle encountered by the torsional bit force, $\theta_r$, at angle $\eta$ is defined as:

$$\theta_r = \pi/2 - \theta|\eta - \eta_d|2/\pi \tag{70}$$

Since $\eta_d$ has a valid range of $-\pi/2 \leq \eta_d \leq \pi/2$, $\eta$ should be constrained within the following range: $(\eta_d - \pi/2) \leq \eta \leq (\eta_d + \pi/2)$, or using computer logic:

If $\eta > (\eta_d + \pi/2)$ then: $\eta = \eta - \pi$ \hfill (71)

The intermediate rock compressive strength so computed above, $\sigma_{1ri}$, must then be reduced by an amount defined by the confinement stress acting in the direction of $u_{\sigma 1r}$. The result, $\sigma_{1r}$, is the in-situ rock strength opposing the circumferential bit force at the point of interest and may be expressed as:

$$\sigma_{1r} = \sigma_{1ri} - |(\sigma_h u_h + \sigma_v u_v + \sigma_g u_g) \cdot u_{\sigma 1r}| \tag{72}$$

$\sigma_{1ri}$ is a special case of the equation for a cumulative series from the above assays so that $\sigma_{1r}$ is a modified form of such cumulative series, adjusted for local forces affecting the basic compressive strength. It may also be viewed as an incremental compressive strength in the circumferential direction.

In eq. (72) note that $u_h$ acts in the direction of $u_{\sigma 1r}$ (i.e. $u_h$ has the same i and j components as $u_{\sigma 1r}$). The absolute value of each component is summed as the summation is bidirectional.

The rock strength opposing the axial bit force is obtained in a similar manner. Unit vectors describing the directions of $\sigma_{1a}$, $\sigma_{2a}$, and $\sigma_{3a}$ are obtained at the point of interest.

A unit vector $u_{\sigma 1a}$ describing the direction of $\sigma_{1a}$, the rock strength opposing the axial bit force, at the point of interest may be determined as follows:

$$u_{\sigma 1a} = u_{\sigma 3r} \tag{73}$$

Unit vectors $u_{\sigma 2a}$ and $u_{\sigma 3a}$ describing the directions of $\sigma_{2a}$ and $\sigma_{3a}$, the orthogonal confinement stresses accompanying the axial bit force, at the point of interest are defined as follows:

$$u_{\sigma 2a} = u_{\sigma 2r} \tag{74}$$

$$u_{\sigma 3a} = u_{\sigma 1r} \tag{75}$$

The confinement stress at the point of interest may be obtained by projecting all appropriate confinement stresses in the directions defined by $u_{\sigma 2a}$ and $u_{\sigma 3a}$, and then summing all of the scalar components in each direction. The confinement stress is then the lesser of these two vectorial stress summations, since the confinement stress is always defined by the minimum principal stress. One of these confinement stresses $\sigma_{2a}$ may be determined as follows:

$$\sigma_{2a} = |(\sigma_h u_h + \sigma_v u_v + \sigma_g u_g) \cdot u_{\sigma 2a}| \tag{76}$$

In eq. (76) note that $u_h$ acts in the direction of $u_{\sigma 2a}$ (i.e. $u_h$ has the same i and j components as $u_{\sigma 2a}$). The absolute value of each component is summed as the summation is bidirectional.

The other orthogonal confinement stress $\sigma_{3a}$ is:

$$\sigma_{3a} = |(\sigma_h u_h + \sigma_v u_v + \sigma_g u_g) \cdot u_{\sigma 3a}| \tag{77}$$

In eq. (77) note that $u_h$ acts in the direction of $u_{\sigma 3a}$ (i.e. $u_h$ has the same i and j components as $u_{\sigma 3a}$). The absolute value of each component is summed as the summation is bidirectional. The in-situ rock compressive strength is then computed using the minimum confinement stress just determined above and the relative dip angle defined by angle $\eta$. The relative dip angle encountered by the axial bit force, $\theta_a$, at angle $\eta$ is defined as:

$$\theta_a = \theta \tag{78}$$

The intermediate rock compressive strength so computed above, $\sigma_{1ai}$, must then be reduced by an amount defined by the confinement stress acting in the direction of $u_{\sigma 1a}$. The result, $\sigma_{1a}$, is the in-situ rock strength opposing the axial bit force at the point of interest and may be expressed as:

$$\sigma_{1a} = \sigma_{1ai} - \sigma_b - (\sigma_h u_h + \sigma_v u_v + \sigma_g u_g) \cdot u_{\sigma 1a} \tag{79}$$

$\sigma_{1ai}$ is a special case of the equation for a cumulative series from the above assays so that $\sigma_{1a}$ is a modified form of such cumulative series, adjusted for local forces affecting the basic compressive strength. It may also be viewed as an incremental compressive strength in the axial direction.

In eq. (79) note that $u_h$ acts in the direction of $u_{\sigma 1a}$ (i.e. $u_h$ has the same i and j components as $u_{\sigma 1a}$). The matrix stresses and the overbalance are subtracted from $\sigma_{1ai}$. Note that only the positive components of the vector projections are summed in the direction of $u_{\sigma 1a}$ because the negative components are replaced by the fluid pressure term $\sigma_b$ (i.e. all negative components are discarded).

The rock strength opposing the lateral bit force is obtained in a similar manner. Unit vectors describing the directions of $\sigma_{1L}$, $\sigma_{2L}$, and $\sigma_{3L}$ are obtained at the point of interest. This point of interest is defined by angle $\eta$.

A unit vector $u_{\sigma 1L}$ describing the direction of $\sigma_{1L}$, the rock strength opposing the lateral bit force, at the point of interest may be expressed as follows:

$$u_{\sigma 1L} = u_{\sigma 2r} \tag{80}$$

Unit vectors $u_{\sigma 2L}$ and $u_{\sigma 3L}$ describing the directions of $\sigma_{2L}$ and $\sigma_{3L}$, the orthogonal confinement stresses accompanying the lateral bit force, at the point of interest are defined as follows:

$$u_{\sigma 2L} = u_{\sigma 3r} \tag{81}$$

$$u_{\sigma 3L} = u_{\sigma 1r} \tag{82}$$

The confinement stress at the point of interest may be obtained by projecting all appropriate confinement stresses in the directions defined by $u_{\sigma 2L}$ and $u_{\sigma 3L}$, and then summing all of the scalar components in each direction. The confinement stress is then the lesser of these two vectorial stress summations, since the confinement stress is always defined by the minimum principal stress. One of these confinement stresses $\sigma_{2L}$ may be determined as follows:

$$\sigma_{2L} = |(\sigma_h u_h + \sigma_v u_v + \sigma_g u_g) \cdot u_{\sigma 2L}| \tag{83}$$

In eq. (83) note that $u_h$ acts in the direction $u_{\sigma 2L}$ (i.e. $u_h$ has the same i and j components as $u_{\sigma 2L}$). The absolute value of each component is summed as the summation is bi-directional.

The other orthogonal confinement stress $\sigma_{3L}$ is:

$$\sigma_{3L}=|(\sigma_h u_h+\sigma_v u_v+\sigma_g u_g)\cdot u_{\sigma 3L}| \qquad (84)$$

In eq. (84) note that $u_h$ acts in the direction of $u_{\sigma 3L}$ (i.e. $u_h$ has the same i and j components as $u_{\sigma 3L}$). The absolute value of each component is summed as the summation is bidirectional. The in-situ rock compressive strength is then computed using the minimum confinement stress just determined above and the relative dip angle defined by angle $\eta$.

The relative dip angle encountered by the lateral bit force, $\theta_L$, at angle $\eta$ is defined as:

$$\theta_L=\pi/2-\theta(1-|\eta-\eta_a|2/\pi) \qquad (85)$$

$\eta$ should be constrained as described above in eq. (71).

The intermediate rock compressive strength so computed above, $\sigma_{1Li}$, must then be reduced by an amount defined by the confinement stress acting in the direction of $u_{\sigma 1L}$. The result, $\sigma_{1L}$, is the in-situ rock strength opposing the lateral bit force at the point of interest and may be expressed as:

$$\sigma_{1L}=\sigma_{1Li}-\sigma_b-(\sigma_h u_h+\sigma_v u_v+\sigma_g u_g)\cdot u_{\sigma 1L} \qquad (86)$$

$\sigma_{1Li}$ is a special case of the equation for a cumulative series from the above assays so that $\sigma_{1L}$ is a modified form of such cumulative series, adjusted for local forces affecting the basic compressive strength. It may also be viewed as an incremental compressive strength in the lateral direction.

In eq. (86) note that $u_h$ acts in the direction of $u_{\sigma 1L}$ (i.e. $u_h$ has the same i and j components as $u_{\sigma 1L}$). The matrix stresses and the overbalance are subtracted from $\sigma_{1Li}$. Note that only the positive components of the vector projections are summed in the direction of $u_{\sigma 1L}$ because the negative components are replaced by the fluid pressure term $\sigma_b$ (i.e. all negative components are discarded).

Substituting $\sigma_{1r}$, $\sigma_{1a}$ and $\sigma_{1t}$ into equation (54), we can get compressive strength at the point of interest.

Average values for $\sigma_{1r}$ and $\sigma_{1L}$, may be obtained by repeating the above process for multiple points on the rock annulus using respective $\eta$'s, and then averaging the results. There are many ways to accomplish this task. The number of points can be minimized through careful selection. In addition it is desirable to determine the points where maximum and minimum values occur for wellbore stability analysis. If the minimum values approach zero, wellbore instability (i.e. "cave-ins") is likely. For $\sigma_{1a}$, we again repeat for other points, but use the minimum $\sigma$ for these, rather than an average.

Finally, we use these averages and minimum with equation (54) to get the in-situ compressive strength for the site.

In other exemplary embodiments, rather than basing the analysis on consideration of individual points about the circumference of the site, one might use averages of the confinement stresses (circumferential, axial and lateral) and the average relative dip angle to produce a compressive strength signal for the entire annular site, which compressive strength signal is, itself, an average.

As mentioned above, the modeling may be done in advance of drilling using data from adjacent wellbore 52. In addition, because the physical data needed to do this modeling are typically easily obtainable during a drilling process, the modeling may also be done in real time, either instead of, or in addition to, the advance modeling. A highly preferred method would be to use the advance modeling for initial guidance, but modify the drilling plan developed therefrom, as indicated, if real time modeling indicates sufficient differences, which could occur if the locus l passes through rock of different characteristics than that of the adjacent wellbore 52.

We claim:

1. A method of assaying the compressive strength of rock comprising the steps of:

testing a primary plurality of rock samples of similar lithology, at least some of which have different porosities, to determine, for each sample respectively, a compressive strength and a porosity;

generating a first series of pairs of electrical compressive strength and porosity signals, the signals of each pair corresponding, respectively, to the compressive strength and porosity for a respective one of said samples; and processing the compressive strength and porosity signals to extrapolate additional such pairs of signals and generate a second series of electrical signals corresponding to compressive strength as a function of porosity.

2. The method of claim 1 wherein said processing includes bounding said second series by an electrical maximum porosity signal corresponding to a maximum value for porosity.

3. The method of claim 2 comprising iteratively processing electrical signals potentially corresponding to: said maximum value for porosity and a paired value for a minimum unconfined compressive strength, a value for a maximum unconfined compressive strength, and a mineralogical value for the lithology, to generate multiple potential second series;

and using as said second series the potential second series corresponding to a function whose graphical representation is a logarithmic decline most nearly fitting the upper periphery of a cloud of data points corresponding to said first series of signals on a Cartesian graph of compressive strength versus porosity.

4. The method of claim 3 wherein the compressive strength so determined for each of said samples is an unconfined compressive strength.

5. The method of claim 4 comprising so processing to generate said second series such that said second series corresponds to a function of the form:

$$\sigma_u=S_e\sigma_{umax}+(1-S_e)\sigma_{umin}$$

where:

$S_e=(1-\phi/\phi_{max})^\alpha$
 = effective solidity $\sigma_u$ = said unconfined compressive strength $\sigma_{umax}$ = said maximum unconfined compressive strength $\sigma_{umin}$ = said minimum unconfined compressive strength $\phi$ = porosity $\phi_{max}$ = said maximum porosity $\alpha$ = said mineralogy value.

6. The method of claim 3 comprising generating a plurality of electrical adjustment signals corresponding to values of at least one other condition affecting the compressive strength of lithologically similar rock; and processing said adjustment signals to generate a cumulative series of electrical signals corresponding to adjusted compressive strength as a function of porosity and said other condition.

7. The method of claim 6 comprising generating at least some of said adjustment signals as stress adjustment signals corresponding to functions of changes in rock strength due to confinement stress.

8. The method of claim 7 wherein the generation of said stress adjustment signals includes testing a secondary plurality of rock samples of similar lithology to the primary samples, and at least some of which have different porosities, under laterally confined conditions, to determine for each of said other samples, respectively, a confined compressive strength and a porosity;

generating a third series of pairs of electrical confined compressive strength and porosity signals, the signals of each such pair corresponding, respectively, to the confined compressive strength and porosity for a respective one of said secondary samples;

processing the confined compressive strength and porosity signals of said third series to extrapolate additional such pairs of signals and generate a fourth series of electrical signals corresponding to confined compressive strength as a function of porosity.

9. The method of claim 8 wherein said processing of said third series includes bounding said fourth series by an electrical maximum porosity signal corresponding to a maximum value for porosity.

10. The method of claim 9 further comprising so generating a plurality of alternative such fourth series, each of said alternative fourth series from respective samples so tested at a respective lateral confining force;

using the signals of said plurality of alternative fourth series to determine a principal stress relationship value;

generating an electrical signal corresponding to said principle stress relationship value;

and processing said signal corresponding to the principle stress relationship value to generate said cumulative series of signals.

11. The method of claim 7 comprising generating others of said adjustment signals as orientation adjustment signals corresponding to changes in compressive strength due to dip angle of a bedding plane of the rock.

12. The method of claim 11 comprising testing at least two sub-sets of a tertiary plurality of rock samples of similar lithology, the samples of each sub-set having different dip angles with respect to horizontal but the same porosity, to determine, for each of said tertiary samples, a set of orientation variables; the generation of said orientation adjustment signals including first generating a plurality of electrical orientation variable signals corresponding, respectively, to said orientation variables, the orientation variables occurring in pairs, one pair for each sample, and the orientation variables of each pair corresponding, respectively, to relative dip angle and compressive strength.

13. The method of claim 12 wherein the porosities of said two subsets of tertiary rock samples differ.

14. The method of claim 13 comprising processing said orientation variable signals to generate signals corresponding to the orientation variables at maximum porosity and minimum porosity for said lithology.

15. The method of claim 14 comprising processing said orientation variable signals to generate intermediate orientation signals to correspond, respectively, to:

$\theta$=dip angle relative to a prospective borehole axis $f_1$=a maximum percent reduction in compressive strength, at $\theta_c$ and zero porosity, due to dip angle, $f_2$=a maximum percent reduction in compressive strength at $\theta_c$ and maximum porosity, due to dip angle, $f_3$=a maximum percent increase in compressive strength at $\theta=90°$ and zero porosity, due to dip angle, $f_4$=a maximum percent increase in compressive strength at $\theta=90°$ and maximum porosity, due to dip angle.

n=an orientation value for the lithology;

where:

$\theta_c$=a critical dip angle at which compressive strength is minimum.

16. The method of claim 15 wherein said intermediate orientation signals are processed to generate said orientation adjustment signals;

said orientation adjustment signals corresponding to a maximum orientation adjustment value (at minimum porosity), and a minimum orientation adjustment value (at maximum porosity).

17. The method of claim 16 comprising generating additional signals corresponding, respectively, to:

$\gamma$=a sine function of $\theta$, having a maximum value of 90° at $\theta=\theta_c$, $\sigma_\theta$=compressive strength at $\theta$;

where:

for $0<\theta\leq\theta_c$:

$\gamma=(\theta/\theta_c)\pi/$ $f_1=(\sigma_{\theta=0}-\sigma_{\theta=0})$, at minimum porosity $f_2=f_1$, at maximum porosity $c_{omax}=f_1 \sin^n (\gamma)$ $c_{omin}=f_2 \sin^n (\gamma)$ and for $\theta_c<\theta\leq 90°$:

$\gamma=\pi/2+(\theta-\theta_c)/1-\theta_c 2/\pi)$ $f_3=(\sigma_{\theta=90°}-\sigma_{\theta=0})/\sigma_{\theta=0}$, at minimum porosity $f_4=f_3$, at maximum porosity $c_{omax}=f_1+f_3 \sin^n (\gamma)-f_3$ $c_{omin}=f_2+f_4 \sin^n (\gamma)-f_4$ and where:

$c_{omax}$=said maximum orientation adjustment value (at minimum porosity)

$c_{omin}$=said minimum orientation adjustment value (at maximum porosity)

and so processing said intermediate variable signals with said additional signals.

18. The method of claim 11 comprising generating said adjustment signals also as temperature adjustment signals corresponding to functions of changes in compressive strength due to temperature.

19. The method of claim 18 comprising testing a plurality of sub-sets of a quaternary plurality of rock samples of similar lithology, the samples of each sub-set having the same porosity and confining stress but being tested at different temperatures, to determine, for each of said quaternary samples, a set of temperature variables; the generation of said temperature adjustment signals including first generating a plurality of electrical temperature variable signals occurring in pairs, the signals of each pair corresponding, respectively, to compressive strength and temperature for a respective quaternary sample.

20. The method of claim 19 wherein some of the subsets of quaternary samples have a first, relatively low, porosity, but differ, one subset from the other, in confinement stress; and others of said subsets of quaternary rock samples have a second, relatively high porosity, but differ, one subset from another, as to confinement stress.

21. The method of claim 20 comprising processing said temperature variable signals to generate signals corresponding to the temperature variables at maximum porosity and minimum porosity for said lithology.

22. The method of claim 21 comprising processing said temperature variable signals to generate intermediate temperature signals to correspond, respectively, to:

$f_5$=percent reduction in compressive strength at maximum test temperature and maximum test confining stress ($T=T_{max}$, $\sigma_3=\sigma_{3max}$), at maximum porosity ($\phi=\phi_{max}$)

$f_6$=percent reduction in compressive strength at maximum test temperature and standard pressure (T=$T_{max}$, $\sigma_3$=0), at maximum porosity ($\phi=\phi_{max}$)

$f_7$=percent reduction in compressive strength at maximum test temperature and maximum test confinement stress (T=$T_{max}$, $\sigma_3=\sigma_{3max}$), at zero porosity ($\phi$=0)

$f_8$=percent reduction in compressive strength at maximum test temperature and standard pressure (T=$T_{max}$, $\sigma_3$=0), at zero porosity ($\phi$=0)

a=a pressure-strength relationship value b=a temperature-strength relationship value.

23. The method of claim 22 wherein said intermediate temperature signals are processed to generate said temperature adjustment signals;

said temperature adjustment signals corresponding to a maximum temperature adjustment value (at minimum porosity), and a minimum temperature adjustment value (at maximum porosity).

24. The method of claim 6 comprising so generating said adjustment signals by processing at least some of said porosity signals.

25. The method of claim 24 comprising so generating at least some of said adjustment signals as stress adjustment signals corresponding to changes in rock strength due to confinement stress.

26. The method of claim 25 comprising so generating others of said adjustment signals as orientation adjustment signals corresponding to changes in compressive strength due to dip angle of a bedding plane of the rock.

27. The method of claim 26 further comprising so generating still others of said adjustment signals as temperature adjustment signals corresponding to changes in compressive strength due to temperature.

28. The method of claim 27 comprising so generating said temperature adjustment signals as a function of at least some of said stress adjustment signals.

29. The method of claim 24 comprising so generating at least some of said adjustment signals as orientation adjustment signals corresponding to changes in compressive strength due to dip angle of a bedding plane of the rock.

30. The method of claim 24 further comprising so generating at least some of said adjustment signals as temperature adjustment signals corresponding to changes in compressive strength due to temperature.

31. The method of claim 6 comprising so generating said adjustment signals by generating and processing signals corresponding to physical properties characterizing changes in compressive strength due to confinement stress, orientation, and temperature.

32. The method of claim 31 comprising:

repeating said assaying method for at least one other lithology;

additionally determining site characteristics of the rock for a wellbore locus, at a plurality of sites along the length of said locus, and as the rock would be addressed by a drill bit, said site characteristics including porosity and physical properties similar to those so used to generate said adjustment signals, the site characteristics for each site also including values corresponding to the relative percentages of the lithologies so assayed at said site;

generating a plurality of site signals corresponding, respectively, to said site characteristics;

and processing the site signals for each site with the cumulative series of signals to generate in-situ compressive strength signals corresponding to the in-situ compressive strengths of the rock at each site.

33. The method of claim 32 comprising, for each such site, generating an electrical wellbore angle signal corresponding to the wellbore inclination angle, an electrical wellbore azimuth signal corresponding to the wellbore azimuth, an electrical bed plane angle signal corresponding to the dip angle with respect to the earth, and an electrical bed plane dip azimuth signal corresponding to the dip azimuth;

and processing said wellbore angle, wellbore azimuth, bed plane angle, and bed plane dip azimuth signals to generate an electrical relative dip angle signal corresponding to a relative dip angle of the bed plane with respect to the borehole at the respective site;

and so processing said relative dip angle signal with the cumulative series.

34. The method of claim 32 comprising generating one of the site signals as an in-situ confining stress signal corresponding to in-situ confining stress.

35. The method of claim 34 wherein said in situ confining stress signal is generated by processing a signal corresponding to effective stress due to the pressure differential between fluid in the wellbore and fluid in the surrounding formation.

36. The method of claim 34 wherein said in-situ confining stress signal is also generated by processing a signal corresponding to effective stress due to overburden.

37. The method of claim 36 wherein said in-situ confining stress signal is also generated by processing an electrical signal corresponding to effective stress due to the local geological stress field.

38. The method of claim 32 comprising so generating at least some of said site signals by processing circumferential signals corresponding to stress, other than that applied by the drill bit, acting circumferentially on the rock at the respective site.

39. The method of claim 38 comprising so generating at least some of said circumferential signals to correspond to effective stress due to the pressure differential between fluid in the wellbore and fluid in the surrounding formation.

40. The method of claim 39 comprising so generating some of said circumferential signals to correspond to effective circumferential stress due to overburden.

41. The method of claim 40 comprising so generating some of said circumferential signals to correspond to effective circumferential stress due to the local geological stress field.

42. The method of claim 38 comprising so generating at least some of said site signals by processing axial signals corresponding to axial stress, other than that applied by the drill bit, acting axially on the rock at the respective site.

43. The method of claim 42 comprising so generating at least some of said axial signals to correspond to the pressure differential between fluid in the wellbore and fluid in the surrounding formation.

44. The method of claim 43 comprising so generating some of said axial signals to correspond to effective axial stress due to overburden.

45. The method of claim 44 comprising so generating some of said axial signals to correspond to effective stress due to the local geological stress field.

46. The method of claim 42 comprising so generating at least some of said site signals by processing lateral signals corresponding to lateral stress, other than that applied by the drill bit, acting laterally on the rock at the respective site.

47. The method of claim 46 comprising so generating at least some of said lateral signals to correspond to effective lateral stress due to the pressure differential between fluid in the wellbore and fluid in the surrounding formation.

48. The method of claim 47 further comprising so generating some of said lateral signals to correspond to effective lateral stress due to overburden.

49. The method of claim 48 comprising so generating some of said lateral signals to correspond to effective lateral stress due to the local geological stress field.

50. The method of claim 34 including generating an incremental in situ compressive strength signal corresponding to the compressive strength at a point on an annulus of rock perpendicular to the wellbore at said site in one of three mutually orthogonal directions, circumferential, axial, or lateral, with respect to the wellbore axis.

51. The method of claim 50 comprising so generating said incremental in-situ compressive strength signal by processing an incremental confinement stress signal corresponding to the lesser of the stresses acting on said point in the other two of said mutually orthogonal directions.

52. The method of claim 51 wherein said generation of said incremental in situ compressive strength signal further comprises processing of signals corresponding to forces, other than applied by the drill bit, acting parallel to said one direction.

53. The method of claim 52 comprising so generating another such incremental in-situ compressive strength signal for a second of said three directions.

54. The method of claim 53 comprising so generating a third such incremental in-situ compressive strength signal for the third of said directions.

55. The method of claim 54 comprising so generating additional incremental in-situ compressive strength signals for other points on said annulus, and processing said incremental compressive strength signals to generate said in-situ compressive strength signal.

56. The method of claim 6 comprising the additionally step of determining site characteristics of the rock for a wellbore locus, at a plurality of sites along the length of said locus, and as the rock would be addressed by a drill bit, said site characteristics including porosity and physical properties similar to those so used to generate said adjustment signals;

generating a plurality of site signals corresponding, respectively, to said site characteristics;

and processing said site signals with said cumulative series of signals to generate in-situ compressive strength signals corresponding to the in-situ compressive strengths of the rock at the respective sites.

57. The method of claim 56 wherein said site characteristics are estimated, based on data from a well near said locus, and said in-situ compressive strength signals are advance in-situ compressive strength signals so generated before drilling a well along said locus.

58. The method of claim 57 comprising generating and at least partially executing a plan for drilling said well based on values corresponding to said advance in-situ compressive strength signals; and re-evaluating said site characteristics while said drilling of said well is in progress, based on real time data for said site characteristics;

so generating a corresponding plurality of real time site signals;

so processing said real time site signals with said cumulative series of signals to generate real time in-situ compressive strength signals; and revising said plan when the real time compressive strength signal for a given site differs sufficiently from the advance compressive strength signal for the same site.

59. The method of claim 56 comprising drilling a wellbore along said locus and so determining said site characteristics on the basis of real time data acquired while so drilling.

60. The method of claim 1 comprising the additionally step of determining site characteristics of the lithology for a wellbore locus, at a plurality of sites along the length of said locus, and as the lithology would be addressed by a drill bit, said site characteristics including porosity;

generating a plurality of site signals corresponding, respectively, to said site characteristics;

and processing said site signals with said second series of signals to generate in-situ compressive strength signals corresponding to the in-situ compressive strengths of the lithology at the respective sites.

* * * * *